United States Patent
Barbic et al.

(10) Patent No.: US 11,798,232 B2
(45) Date of Patent: *Oct. 24, 2023

(54) METHOD AND SYSTEM FOR GENERATING A NEW ANATOMY

(71) Applicant: Ziva Dynamics Inc., Vancouver (CA)

(72) Inventors: Jernej Barbic, Santa Monica, CA (US);
Essex Edwards, Vancouver (CA);
James Jacobs, Vancouver (CA);
Crawford Doran, Vancouver (CA)

(73) Assignee: Ziva Dynamics Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/681,530

(22) Filed: Feb. 25, 2022

(65) Prior Publication Data

US 2022/0180607 A1 Jun. 9, 2022

Related U.S. Application Data

(63) Continuation of application No. 16/635,979, filed as application No. PCT/CA2018/050951 on Aug. 2, 2018, now Pat. No. 11,288,866.

(Continued)

(51) Int. Cl.
*G06T 17/20* (2006.01)
*G06T 19/20* (2011.01)

(52) U.S. Cl.
CPC ............ *G06T 17/205* (2013.01); *G06T 19/20* (2013.01); *G06T 2219/2008* (2013.01)

(58) Field of Classification Search
None
See application file for complete search history.

(56) References Cited

U.S. PATENT DOCUMENTS 6,643,385 B1 11/2003 Bravomalo
9,898,858 B2 2/2018 Tamersoy et al.
(Continued)

FOREIGN PATENT DOCUMENTS

WO WO-2019023808 A1 2/2019

OTHER PUBLICATIONS

Scheepers, Ferdi, et al. "Anatomy-based modeling of the human musculature." Proceedings of the 24th annual conference on Computer graphics and interactive techniques. 1997. (Year: 1997).*

(Continued)

*Primary Examiner* — Ryan M Gray
(74) *Attorney, Agent, or Firm* — Schwegman Lundberg & Woessner, P.A.

(57) ABSTRACT

Methods, systems, and techniques for generating a new anatomy use a processor to obtain a skin mesh of the new anatomy that is in correspondence with a skin mesh of a template anatomy; after obtaining the skin mesh, transfer a fascia mesh of the template anatomy to the new anatomy; and after the fascia mesh is transferred, generate a fat displacement field defining fat of the new anatomy. The displacement field includes multi-dimensional displacement vectors, and each of the displacement vectors relates a vertex of the skin mesh of the new anatomy to a corresponding vertex of the fascia mesh of the new anatomy. A new anatomy may also be generated by interpolating from anatomies in a database.

20 Claims, 10 Drawing Sheets

Related U.S. Application Data

(60) Provisional application No. 62/540,539, filed on Aug. 2, 2017.

(56) References Cited

U.S. PATENT DOCUMENTS

| | | | |
|---|---|---|---|
| 11,288,866 | B2* | 3/2022 | Barbic ................ G06T 17/20 |
| 2003/0184544 | A1 | 10/2003 | Prudent |
| 2009/0135189 | A1 | 5/2009 | Kim et al. |
| 2015/0379744 | A1 | 12/2015 | Kretschmer et al. |
| 2016/0005106 | A1* | 1/2016 | Giraldez ............ G06Q 30/0277 705/27.2 |
| 2021/0142563 | A1 | 5/2021 | Barbic et al. |

OTHER PUBLICATIONS

Turner, Russell, and Enrico Gobbetti. "Interactive construction and animation of layered elastically deformable characters." Computer Graphics Forum. vol. 17. No. 2. Oxford, UK and Boston, USA: Blackwell Publishers, 1998. (Year: 1998).*

Aubel, Amaury, and Daniel Thalmann. "Realistic deformation of human body shapes." Computer Animation and Simulation 2000: Proceedings of the Eurographics Workshop in Interlaken, Switzerland, Aug. 21-22, 2000. Springer Vienna, 2000. (Year: 2000).*

Guo, Zheng, and Kok Cheong Wong. "Skinning with deformable chunks." Computer Graphics Forum. vol. 24. No. 3. Oxford, UK and Boston, USA: Blackwell Publishing, Inc, 2005. (Year: 2005).*

U.S. Appl. No. 16/635,979, Non Final Office Action dated Mar. 26, 2021, 16 pgs.

U.S. Appl. No. 16/635,979, Notice of Allowance dated Nov. 16, 2021, 7 pgs.

U.S. Appl. No. 16/635,979, Preliminary Amendment dated Jan. 31, 2020, 11 pgs.

U.S. Appl. No. 16/635,979, Response filed Sep. 24, 2021 to Non Final Office Action dated Mar. 26, 2021, 13 pgs.

International Application Serial No. PCT/CA2018/050951, International Preliminary Report on Patentability dated Feb. 13, 2020, 11 pgs.

International Application Serial No. PCT/CA2018/050951, International Search Report dated Oct. 12, 2018, 3 pgs.

International Application Serial No. PCT/CA2018/050951, Written Opinion dated Oct. 12, 2018, 9 pgs.

Allen, Brett, et al., "The space of human body shapes: reconstruction and parameterization from range scans", ACM SIGGRAPH 2003, (2003), 8 pgs.

Besl, P. J, et al., "A Method for Registration of 3-D Shapes", IEEE Transactions on Pattern Analysis and Machine Intelligence, 14 (2), (Feb. 1992), 239-256.

Ersotelos, Nikolaos, et al., "Building highly realistic facial modeling and animation: a T survey", The Visual Computer 24.1, (2008), 13-30.

Jacobson, Alec, et al., "Bounded Biharmonic Weights for Real-time Deformation", ACM Trans. Graph. 30(4), (2011), 8 pgs.

Jun, Li, et al., "Creating real body model of dressed human based on fat extent of body", Multimedia Tools and Applications 7 4.17, (2015), 6951-6966.

Saito, Shunsuke, et al., "Computational Bodybuilding: Anatomically-based Modeling of Human Bodies", ACM Transaction on Graphics 34(4), Proceedings of SIGGRAPH, (2015), 12 pgs.

Seo, Hyewon, et al., "Synthesizing animatable body models with parameterized shape modifications", Proceedings of the 2003 ACM SIGGRAPH/Eurographics symposium on Computer animation, (2003).

Shepard, Donald, "A two-dimensional interpolation function for irregularly-spaced data", Proceedings of the 1968 ACM National Conference, (1968), 517-524.

Turchet, Fabio, et al., "Extending implicit skinning with wrinkles", Proceedings of the 12th European, Conference on Visual Media Production, (2015).

Wang, Haining, et al., "Survey: Parameterized 3d human body modeling and geometric deformation technology", 2009 IEEE 10th International Conference on Computer-Aided Industrial Design & Conceptual Design. IEEE, (2009).

Wang, Yu, et al., "Linear Subspace Design for Real-Time Shape Deformation", ACM Transactions on Graphics 34(4) (SIGGRAPH 2015), Los Angeles, CA, USA, (2015), 11 pgs.

* cited by examiner

METHOD AND SYSTEM FOR GENERATING A NEW ANATOMY

CROSS REFERENCE TO RELATED APPLICATIONS

This application is a continuation of and claims the benefit of priority under 35 U.S.C. § 120 to U.S. patent application Ser. No. 16/635,979, filed on Jan. 31, 2020, which is a U.S. National Stage Filing under 35 U.S.C. 371 from International Application No. PCT/CA2018/050951, filed on Aug. 2, 2018, and published as WO 2019/023808 A1 on Feb. 7, 2019, which claims the benefit of priority under 35 U.S.C. § 119(e) to U.S. Provisional Patent Application No. 62/540,539, filed on Aug. 2, 2017, each of which is incorporated by reference herein in its entirety.

TECHNICAL FIELD

The present disclosure is directed at methods, systems, and techniques for generating a new anatomy.

BACKGROUND

Computer models of humans and animals (these models are "anatomies") are used in a number of industries. As one example, the visual effects industry regularly used anatomies when implementing motion picture special effects. As another example, the gaming industry uses anatomies for visual reality, augmented reality, and mixed reality games. In certain applications, such as in video games and motion pictures it may also be desirable to simulate anatomies' movements.

There accordingly exists a continued need for methods, systems, and techniques for generation anatomies.

SUMMARY

According to a first aspect, there is provided a method for generating a new anatomy, the method comprising using a processor to obtain a skin mesh of the new anatomy that is in correspondence with a skin mesh of a template anatomy, after obtaining the skin mesh, transfer a fascia mesh of the template anatomy so the new anatomy, and after the fascia meth is transferred, generate a fat displacement field defining fat of the new anatomy, wherein the displacement field comprises multi-dimensional displacement vectors and each of the displacement vectors relates a vertex of the skin mesh of the new anatomy to a corresponding vertex of the fascia mesh of the new anatomy.

Obtaining the skin mesh of the new anatomy that is in correspondence with the skin mesh of the template anatomy may comprise using the processor to perform mesh registration of the skin mesh of the new anatomy to the skin mesh of the template anatomy.

The method may further comprise, after the fascia mesh is transferred, transferring a simulation structure of the template anatomy to the new anatomy.

The method may further comprise using the processor to, after the fascia mesh is transferred, transfer bone meshes and muscle meshes of the template anatomy to the new anatomy, wherein the processor transfers the muscle meshes after transferring the bone meshes.

The method may further comprise using the processor to, after the fascia mesh is transferred, transfer bone meshes and muscle meshes of the template anatomy to the new anatomy, wherein the processor treats the bone and muscle meshes identically when transferring the bone and muscle meshes to the new anatomy and concurrently transfers the bone and muscle meshes to the new anatomy.

The method may further comprise after the processor transfers the bone meshes and muscle meshes and generates the displacement field, using the processor to adjust the shape of the fascia mesh of the new anatomy; and after the fascia mesh has been adjusted, adjust the shape of at least one of the bone and muscle meshes of the new anatomy in response to the adjusted shape of the fascia mesh.

The method may further comprise after the processor transfers the bone meshes and muscle meshes and generates the displacement field, using the processor to adjust the shape of at least one of the bone and muscle meshes of the new anatomy; and after the at least one of the bone and muscle meshes has been adjusted, adjust the fascia mesh of the new anatomy in response to the adjusted shape of the at least one muscle mesh.

The topology of the fascia mesh of the new anatomy immediately after adjustment may be identical to the topology of the fascia mesh of the new anatomy immediately before adjustment.

The topology of the fascia mesh of the new anatomy immediately after adjustment may differ from the topology of the fascia mesh of the new anatomy immediately before adjustment, and the method may further comprise using the processor to perform mesh registration of the fascia mesh of the new anatomy immediately after adjustment to the fascia mesh of the new anatomy immediately before adjustment.

The processor may associate with each of the muscle meshes a bodybuilding constant specifying a size of the muscle mesh of the new anatomy relative to a size of a corresponding muscle mesh of the template anatomy, and adjusting the shape of at least one of the muscle meshes of the new anatomy may comprise adjusting the bodybuilding constant of each of the at least one of the muscle meshes.

Each of the muscle meshes may contract and extend along a longitudinal axis and the bodybuilding constant may specify a size of the muscle mesh in a direction transverse to the longitudinal axis.

The method may further comprise after the processor transfers the fascia mesh and generates the fat displacement field, using the processor to parameterize the new anatomy relative to additional anatomies, wherein each of the additional anatomies comprises a skin mesh and a fascia mesh in correspondence with the skin mesh and fascia mesh, respectively, of the new anatomy.

Using the processor to parameterize the new anatomy may comprise generating external parameters parameterizing an exterior of each of the new and additional anatomies by performing principal components analysis on vertex positions of the skin meshes of the new and additional anatomies to determine body eigenvectors for each of the new and additional anatomies.

The additional anatomies and the parameters for the additional anatomies may be stored in a database, and the method may further comprise using the processor to, for each of the additional anatomies, determine an exterior difference between the external parameter of the new anatomy and the external parameter of the additional anatomy; and compare the exterior difference to an external parameter difference threshold. When the external parameter difference threshold for each of the additional anatomies is satisfied, the processor may add the new anatomy to the database.

Each of the additional anatomies may further comprise a fat displacement field defining fat of the additional anatomy, wherein the displacement field comprises multi dimensional displacement vectors and each of the displacement vectors relates a vertex of the skin mesh of the additional anatomy to a corresponding vertex of the fascia mesh of the additional anatomy. Using the processor to parameterize the new anatomy may comprise generating internal parameters parameterizing an interior of each of the new and additional anatomies by performing principal components analysis on the displacement fields of the new and additional anatomies to determine fat eigenvectors for parameterizing the fat of each of the new and additional anatomies.

Each of the additional anatomies may further comprise a fat displacement field defining fat of the additional anatomy, wherein the displacement field comprises multi dimensional displacement vectors and each of the displacement vectors relates a vertex of the skin mesh of the additional anatomy to a corresponding vertex of the fascia mesh of the additional anatomy. Using the processor to parameterize the new anatomy may comprise generating external parameters by parameterizing an exterior of each of the new and additional anatomies by performing principal components analysis on vertex positions of the skin meshes of the new and additional anatomies to determine body eigenvectors for each of the new and additional anatomies; and generating internal parameters by parameterizing an interior of each of the new and additional anatomies by performing principal components analysis on the displacement fields of the new and additional anatomies to determine fat eigenvectors for parameterizing the fat of each of the new and additional anatomies.

The method may further comprise prior to parameterizing the interior of each of the new and additional anatomies, normalizing the fat displacement field of each of the new and additional anatomies relative to the template anatomy by transferring the fascia mesh of each of the new and additional anatomies to the template anatomy and determining the fat displacement field of each of the new and additional anatomies as a difference between the fascia mesh after transfer and the skin mesh of the template anatomy.

The additional anatomies and the parameters for the additional anatomies may be stored in a database, and the method may further comprise using the processor to, for each of the additional anatomies, determine an exterior difference between the external parameter of the new anatomy and the external parameter of the additional anatomy; and compare the exterior difference to an external parameter difference threshold. When the external parameter difference threshold for each of the additional anatomies is satisfied, the processor may add the new anatomy to the database.

The additional anatomies and the parameters for the additional anatomies may be stored in a database, and the method may further comprise using the processor to, for each of the additional anatomies, determine an exterior difference and an interior difference between the external parameter and internal parameter of the new anatomy and the external parameter and internal parameter, respectively, of the additional anatomy; and compare the exterior difference and the interior difference to a combined parameter threshold. When the combined parameter threshold for each of the additional anatomies is satisfied, the processor may add the new anatomy to the database.

The combined parameter difference may weigh the interior and exterior differences differently.

The exterior difference may comprise a weighted Euclidean (L2) distance.

The interior difference may comprise a weighted Euclidean (L2) distance.

The method may further comprise scanning an exterior of a human or animal to generate the skin mesh of at least one of the template anatomy and the new anatomy.

The method may further comprise scanning an interior of a human or animal to generate the fascia mesh of the template anatomy.

According to another aspect, there is provided a method for generating a new anatomy, the method comprising using a processor to access a database storing additional anatomies; and interpolate the new anatomy from the additional anatomies.

The processor interpolating the new anatomy may comprise using the processor to interpolate, from a database of additional anatomies and using an external parameter characterizing an exterior of the new anatomy, vertices of a skin mesh of the new anatomy; interpolate, from the database and an internal parameter characterizing fat of the new anatomy, a fat displacement field of the new anatomy comprising multi-dimensional displacement vectors, wherein each of the displacement vectors relates a vertex of the skin mesh to a corresponding vertex of a fascia mesh of the new anatomy; and determine the fascia mesh of the anatomy by subtracting the fat displacement field from the vertices of the skin mesh.

The processor may interpolate the vertices of the skin mesh using an external starting vector, the external parameter, and body eigenvectors parameterizing exteriors of the additional anatomies; and interpolate the fat displacement field using an internal starting vector, the internal parameter, and fat eigenvectors parameterizing fat of the additional anatomies.

The method may further comprise, after the fascia mesh of the new anatomy is determined, using the processor to transfer muscle and bone meshes from a template anatomy to the new anatomy.

The processor interpolating the new anatomy may comprise using the processor to obtain a skin mesh of the new anatomy that is in correspondence with a skin mesh of a template anatomy; determine an external parameter characterizing an exterior of the new anatomy using vertices of the skin mesh of the new anatomy and body eigenvectors determined using vertices of skin meshes of the additional anatomies; determine an internal parameter characterizing fat of the new anatomy by using regression based on the external parameter; interpolate, from the database and using the external parameter, vertices of an interpolated skin mesh of the new anatomy; interpolate, from the database and using the internal parameter, a fat displacement field of the new anatomy comprising multi-dimensional displacement vectors, wherein each of the displacement vectors relates a vertex of the skin mesh to a corresponding vertex of a fascia mesh of the new anatomy; determine an interpolated fascia mesh of the new anatomy by subtracting the fat displacement field from the vertices of the interpolated skin mesh; and determine the fascia mesh of the new anatomy by transferring the interpolated fascia mesh to the new anatomy.

The method may further comprise, after the fascia mesh of the new anatomy is determined, using the processor to transfer muscle and bone meshes from a template anatomy to the new anatomy.

The processor interpolating the new anatomy may comprises using the processor to obtain a skin mesh of the new anatomy that is in correspondence with a skin mesh of a template anatomy; determine an external parameter characterizing an exterior of the new anatomy using vertices of the skin mesh of the new anatomy and a body eigenvector determined using vertices of skin meshes of additional anatomies in a database; determine k nearest neighbors to the external parameter in the database and weights for the nearest neighbors; determine a weighted external parameter and a weighted internal parameter from the k nearest neighbors and the weights; interpolate, from the database and using the weighted external parameter, vertices of an interpolated skin mesh of the new anatomy; interpolate, from the database and using the weighted internal parameter, a fat displacement field of the new anatomy comprising multi-dimensional displacement vectors, wherein each of the displacement vectors relates a vertex of the skin mesh to a corresponding vertex of a fascia mesh of the new anatomy; determine an interpolated fascia mesh of the new anatomy by subtracting the fat displacement field from the vertices of the interpolated skin mesh; and determine the fascia mesh of the new anatomy by transferring the interpolated fascia mesh to the new anatomy.

The method may further comprise, after the fascia mesh of the new anatomy is determined, using the processor to transfer muscle and bone meshes from a template anatomy to the new anatomy.

The processor interpolating the new anatomy may comprise using the processor to obtain a skin mesh of the new anatomy that is in correspondence with a skin mesh of a template anatomy; determine k nearest neighbors to the skin mesh of the new anatomy and weights for the nearest neighbors; and determine a fascia of the new anatomy by weight summing fascia meshes of the nearest neighbors.

The method may comprise, after the fascia mesh of the new anatomy is determined, using the processor to transfer muscle and bone meshes from a template anatomy to the new anatomy.

The method may further comprise using the processor to determine at least one of bone meshes of the new anatomy by weight summing bone meshes of the nearest neighbors; and muscle meshes of the new anatomy by weight summing muscle meshes of the nearest neighbors.

According to another aspect, there is provided a database storing anatomies, wherein each of the anatomies comprises a skin mesh; a fascia mesh within the skin mesh; and a fat displacement field comprising multi-dimensional displacement vectors, wherein each of the displacement vectors relates a vertex of the skin mesh to a corresponding vertex of the fascia mesh.

According to another aspect, there is provided an anatomy generated according to any of the foregoing methods or suitable variations thereof.

According to another aspect, there is provided a system for generating a new anatomy, the system comprising a display; an input device; a database; a processor communicatively coupled to the display, input device, and database; and a memory communicatively coupled to the processor, the memory having stored thereon computer program code, executable by the processor, which when executed by the processor causes the processor to perform any of the foregoing methods or suitable variations thereof.

According to another aspect, there is provided a non-transitory computer readable medium having stored thereon computer program code, executable by a processor, which when executed by the processor causes the processor to perform any of the foregoing methods or suitable variations thereof.

This summary does not necessarily describe the entire scope of all aspects. Other aspects, features and advantages will be apparent to those of ordinary skill in the art upon review of the following description of specific embodiments.

BRIEF DESCRIPTION OF THE DRAWINGS

In the accompanying drawings, which illustrate one or more example embodiments.

DETAILED DESCRIPTION

In certain applications it may be desirable to be able to generate a personalized anatomy. For example, in the clothing industry a customer may want to generate a personalized anatomy of himself or herself so as to be able to accurately model potential clothing purchases, and to subsequently simulate the anatomy's movement in those potential purchases. As another example, in the visual effects industry, an artist may wish to be able to realistically model and simulate the motion of an actor or actress.

The embodiments described herein are directed at methods, systems, and techniques for generating an anatomy. Different variations are possible in different embodiments. For example, in certain embodiments, the anatomy may be personalized to a particular individual. As another example, in certain embodiments a processor generates the exterior and interior of the anatomy and characterizes the anatomy's fat using multi-dimensional displacement vectors, thereby permitting more realistic simulation than conventional anatomies. Additionally, in certain embodiments the processor parameterizes the exterior and interior of the anatomy relative to anatomies already present in an anatomy database, and uses this parameterization to determine the differences between the generated anatomy and the anatomies already present in that database. If the differences are sufficiently large, the processor adds the anatomy to the anatomy database. By repeating this process, the processor generates a database of anatomies. Further, in certain additional embodiments, the processor interpolates new anatomies from anatomies already present in the anatomy database.

As used herein, an "anatomy" 302 (shown in FIG. 4) means a computer representation of a human or animal; a "personalized anatomy" means an anatomy that is based on a particular human or animal; and a "simulation-ready anatomy" means an anatomy comprising a simulation structure that a processor 610 (shown in FIG. 6 as a central processing unit) may simulate so as to determine one or both of the motion and dynamics of the anatomy 302. The depicted example embodiments use simulation-ready anatomies unless otherwise noted; however, in non-depicted embodiments, anatomies that are not simulation-ready may be used.

Figure 3A:
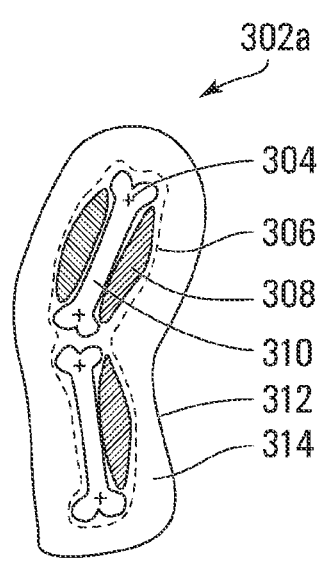
FIGS. 3A-3D depict an example skin mesh, fascia mesh, bone meshes, and muscle meshes during anatomy transfer, according to another example embodiment.
Figure 3B:
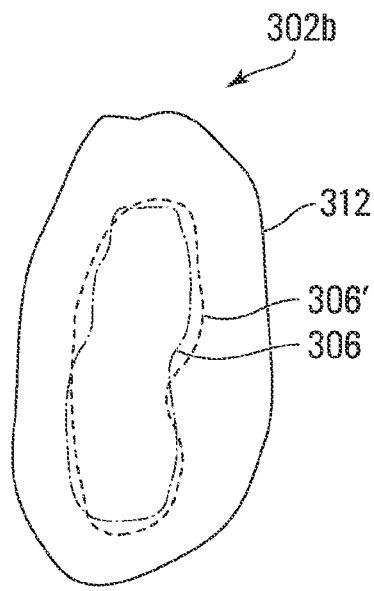
Figure 3C:
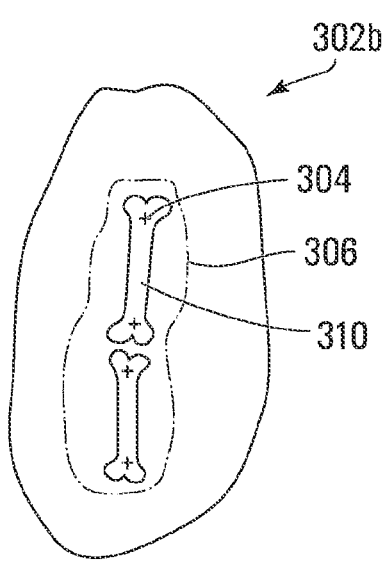
Figure 3D:
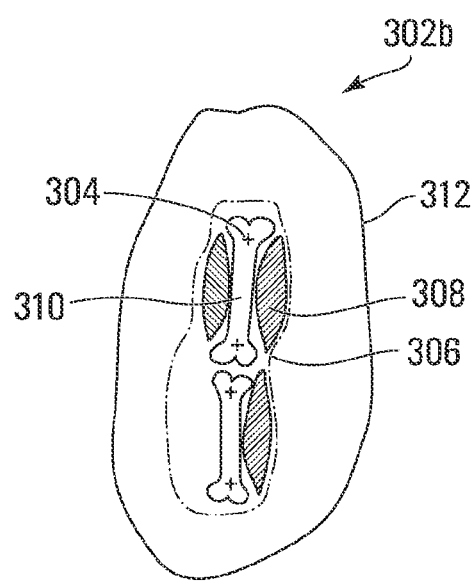
Figure 4:
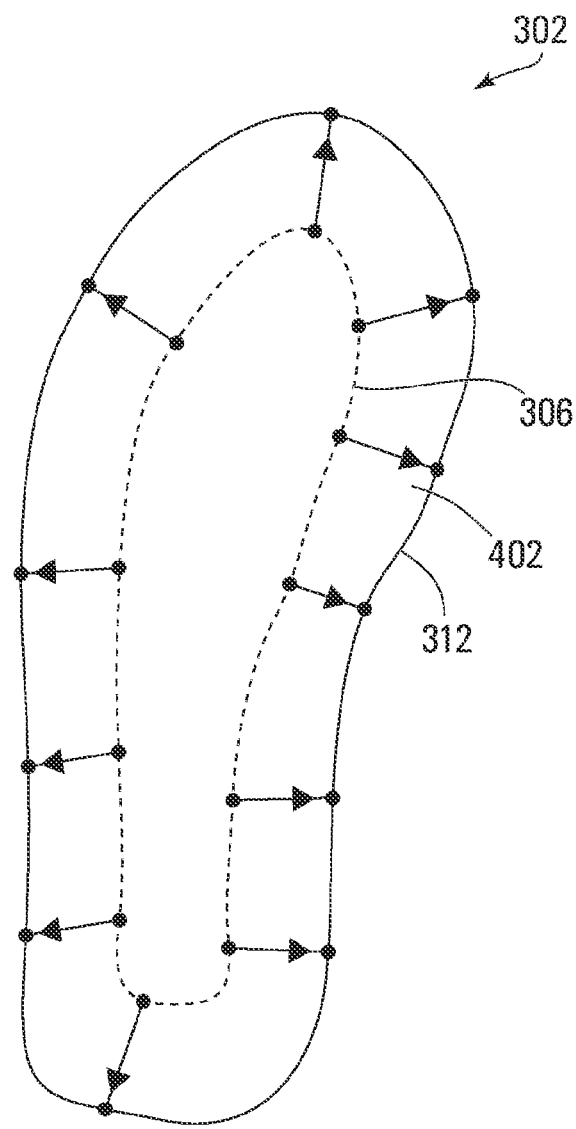
FIG. 4 depicts a fat displacement vector extending between a fascia mesh and a skin mesh, according to another example embodiment.

FIGS. 3A-3D and FIG. 4 depict example components that comprise an anatomy 302. More specifically, FIG. 4 depicts a fat displacement vector 402 that extends between an anatomy's 302 fascia and skin, while FIGS. 3A-3D depict example components that comprise a template anatomy 302a and a new anatomy 302b, each of which is a specific instance of a simulation-ready anatomy 302. The new anatomy 302b is generated using the template anatomy 302a during a process referred to herein as "anatomy transfer", as described in further detail below.

Referring to FIGS. 3A-3D and 4, each anatomy 302 comprises:

1. A polygonal mesh (such as a triangle or quadrilateral mesh) for modeling the anatomy's 302 skin ("skin mesh 312"). The skin mesh 312 is high-detail with a color texture to facilitate rendering. The skin mesh 312 is the anatomy's 302 outermost mesh and contains the anatomy's 302 bones, muscles, and fat. The processor 610 stores in memory 612 (shown in FIG. 6) coordinates defining the position of each vertex of the skin mesh 312.
2. A polygonal mesh that represents the anatomy's 302 fascia and envelops the anatomy's 302 bones and muscles ("fascia mesh 306"). The fascia represents what the anatomy 302 looks like with zero fat. The processor 610 stores in storage the displacement field between the fascia and skin meshes 306,312, sampled as a multi-dimensional displacement vector (each a "fat displacement vector 402", as shown in FIG. 4) between every vertex of the fascia mesh 306 and corresponding vertex of the skin mesh 312. The fat displacement vector 402 in FIG. 4 is three-dimensional, although in other embodiments it is two-dimensional (e.g., when modeling 2D animated characters).
3. Bones, within the fascia mesh 306, defining the anatomy's skeleton. Each bone is modeled as a polygonal mesh ("bone mesh 310").
4. Muscles, located in between the bones and the skin. Each muscle is modeled as a polygonal mesh ("muscle mesh 308"). Often, the muscle meshes 308 are located within the fascia mesh 306, but they may also occupy space in between the fascia and skin meshes 306,312 (e.g., facial muscles). For each muscle mesh 308, the processor 610 also stores in memory 612 a bodybuilding constant specifying how much the muscle mesh 308 has grown or shrunk, relative to the template anatomy's 302a corresponding muscle mesh 308, in a direction transverse to a longitudinal axis along which the muscle mesh 308 contracts and extends.
5. A simulation-ready data structure (an "anatomical rig", not depicted), comprising in one example embodiment the specification of how the muscles and bones are attached to one another (e.g., via attachment stiffness maps, or hard constraints on selected vertices), collision parameters, muscle fiber strengths and simulation-mesh meshing parameters. The processor 610 may perform a simulation using the anatomical rig using three-dimensional solid mechanics, such as by applying the Finite Element Method ("FEM").

To generate the new anatomy 302b, the processor 610 obtains the skin mesh 312 of the new anatomy 302b; after the new anatomy's 302b skin mesh 312 is obtained, transfers the fascia mesh 306 of the template anatomy 302a to the new anatomy 302b; after the fascia mesh 306 is transferred, transfers the bone meshes 310 and muscle meshes 308 of the template anatomy 302a to the new anatomy 302b; and generates a displacement field representing fat of the new anatomy 302b. As mentioned above, the displacement field comprises multi-dimensional displacement vectors 402 and each of the displacement vectors 402 relates a vertex of the new anatomy's 302b skin mesh 312 to a corresponding vertex of the new anatomy's 302b fascia mesh 306. The processor 610 also permits the new anatomy 302b to be adjusted after it is generated. These stages are discussed in more detail below under the headings "Anatomy Transfer" and "Anatomy Adjustment", with one example embodiment being depicted in the flow diagram of FIG. 2.

Prior to commencing anatomy transfer, the processor 610 obtains the new anatomy's 302b skin mesh 312 (block 202). In one example embodiment, this is done by externally scanning (e.g., via MRI) a person other than the person (if any) used to generate the template anatomy 302a. The new anatomy's 302b skin mesh 312 may additionally or alternatively be generated based on biometric information (e.g., height, weight, genetics, body measurements), images, videos, one or both of motion and image capture (such as by using a depth camera 622 [depicted in FIG. 6]), or manually.

The processor 610 also obtains the template anatomy's 302a skin mesh 312 (block 204). The template anatomy's 302a skin mesh 312 in certain embodiments is generated analogously to the new anatomy's 302b skin mesh 312. The processor 610 also obtains the template anatomy's 302a fascia mesh 306, bone meshes 310, and muscle meshes 308 (block 208). These meshes 306,310,308 may be manually modeled, acquired using a 3D internal scan such as an MRI scan, determined using a computerized method such as procedural mesh modeling, or a combination thereof. FIG. 3A depicts an example template anatomy 302a.

Anatomy Transfer

Establish Mesh Correspondence

In the depicted embodiments, the template and new anatomy's 302a,b skin meshes 312 depict identical topologies. The fascia mesh 306 and skin mesh 312 having the same "topology" means that every vertex of the fascia mesh 306 is in 1:1 correspondence with a vertex of the skin mesh 312, thereby permitting the processor 610 to meaningfully sample the fat displacement field between the fascia and the skin meshes 306,312 at the skin mesh's 312 vertices.

In embodiments in which the template and new anatomy's 302a,b skin meshes 312 do not have identical topologies, the processor 610 establishes a correspondence between the meshes 306,312 (block 206). In one embodiment, establishing a correspondence comprises, for each vertex of the skin mesh 306, determining the corresponding location on the fascia mesh 312 using one of several suitable mesh correspondence methods. For example in one embodiment the processor 610 may apply the method described in Besl, Paul J.; N. D. McKay (1992), "A Method for Registration of 3-D Shapes", IEEE Trans. on Pattern Analysis and Machine Intelligence. Los Alamitos, Calif., USA: IEEE Computer Society, 14 (2): 239-256, the entirety of which is hereby incorporated by reference herein.

Transfer Fascia

After establishing mesh correspondence if desired, the processor 610 proceeds to transfer the template anatomy's 302a fascia mesh 306 on to the new anatomy 302b (block 210). To do this, the processor 610 interpolates in the volume enclosed by the template anatomy's 302a skin mesh 312, with boundary conditions given by the deformation between the template anatomy's 302a skin mesh 312 and the new anatomy's 302b skin mesh 312. Specifically, because the template and new anatomies' 302a,b skin meshes 312 are in correspondence, the processor 610 can determine the displacement field at every vertex of the template anatomy's 302a skin mesh 312.

The processor 610 first discretizes the volume enclosed by the template anatomy's 302a skin mesh 312 using a tetrahedral mesh ("tet mesh"). The processor 610 then interpolates the displacement field from the template anatomy's 302a skin mesh's 312 vertices into the interior of the volume the skin mesh 312 encloses, and more specifically, onto the vertices of the tet mesh. The processor 610 separately interpolates the x, y, and z components of the displacement field. In various embodiments, the processor 610 uses either Radial Basis Functions ("RBFs") or Laplace interpolation, for example, to perform the interpolation. RBFs amount to training the kernel centers and their strengths of an RBF network in the volume enclosed by the skin mesh 312, so that the resulting network reconstructs the skin mesh 312 displacements as closely as possible. Laplace interpolation amounts to minimizing the integral of the Laplace operator of the x, y, or z component of the volumetric displacements, over the volume enclosed by the skin mesh 312, subject to the prescribed displacements on the skin mesh 312.

The processor 610 then transfers the template anatomy's 302a fascia mesh 306 onto the new anatomy 302b. The fascia mesh 306 is a polygonal mesh located inside the volume enclosed by the template anatomy's 302a skin mesh 312. For every vertex of the template anatomy's 302a fascia mesh 306, the processor 610 finds which tetrahedron contains it, and uses the displacements of the vertices of that tetrahedron to transfer that fascia vertex to the new anatomy 302b. The processor 610 is accordingly able to define the new anatomy's 302b fat displacement field by determining, for each vertex of the new anatomy's 302b skin mesh 312, the displacement vector 402 to the position of the corresponding fascia mesh 306 vertex.

Following the fascia mesh 306 transfer, the processor 610 has created the new anatomy's 302b skin and fascia meshes 312,306. FIG. 3B depicts an example embodiment in which the template anatomy's 302a fascia mesh 306 has been automatically transferred to the new anatomy 302b as described above using Laplace interpolation; this automatically transferred fascia mesh is labeled 306'. FIG. 3B also depicts another fascia mesh labeled 306, which is the automatically transferred mesh 306' after the user has manually adjusted it to make the new anatomy's 302b fat layer deeper.

Transfer Bones

After transferring the fascia mesh 306, the processor 610 proceeds to transfer the bone meshes 310 from the template anatomy 302a to the new anatomy 302b (block 212).

For each of the template anatomy's 302a bone meshes 310, a user defines multiple bone handles 304 (for complex bones such as a hip), a pair of bone handles 304 at each bone head (for longer bones), or a single bone handle (for shorter bones) 304, as described in Shunsuke Saito, Zi-Ye Zhou, Ladislav Kavan. Computational Bodybuilding. Anatomically-based Modeling of Human Bodies. ACM Transaction on Graphics 34(4) [Proceedings of SIGGRAPH], 2015 ("Saito"), the entirety of which is hereby incorporated by reference herein. Smaller bone meshes 310 each comprising only a single handle 304 may be grouped together. These handles 304 are then used to transfer the bone meshes 310, as described below. In an alternative embodiment (not depicted), the processor 610 may not use the handles 304 at all, but transfer the bone meshes 310 in the same way as the fascia mesh 306, trading quality for speed.

To perform the bone transfer from the template anatomy 302a to the new anatomy 302b using handles 304, the processor 610 first transfers each handle 304. It does so by performing volume interpolation of the displacement field between the template and new anatomies' 302a,b skin meshes 312. Optionally, the processor 610 also includes a constraint that the template anatomy's 302a fascia mesh 306 has to transfer onto the new anatomy's fascia mesh 306. The processor 610 separately interpolates the x, y, and z components of the displacement field at each handle 304. The processor 610 in one embodiment uses Laplace interpolation, and uses RBF interpolation in another embodiment. This results in the processor 610 generating the transferred position of each handle 304 in the new anatomy 302b.

As the handle 304 is located inside the tet mesh of the template anatomy's 302a skin mesh 312, the processor 610 is also able to determine the deformation gradient F at the handle 304, as it is the deformation gradient of the tet mesh. The "deformation gradient" is the three-dimensional gradient of the three-dimensional displacement field, expressed as a 3×3 matrix F. The processor 610 then defines, for each of the handles 304, an affine linear transformation that maps the handle 304 in the template anatomy 302a to its transferred location in the new anatomy 302b, with the transformation having a linear matrix F. This affine transformation gives the first-order Taylor expansion of the volumetric displacement field between the template anatomy's 302a skin mesh 312 and the skin mesh 312 of the new anatomy 302b.

The processor 610 then uses Bounded Bi-harmonic Weights ("BBWs") (see, e.g., Alec Jacobson, Ilya Baran, Jovan Popovic, and Olga Sorkine: Bounded Biharmonic Weights for Real-time Deformation, ACM Trans. Graph. 30(4), 2011, the entirety of which is hereby incorporated by reference herein) for each bone to interpolate the handles' 304 affine transformations to any vertex of the template anatomy's 302a bone meshes 310. The BBWs are scalar weights defined on the surface of each bone mesh 310, and give the relative importance of each handle 304 to each bone mesh 310 vertex; hence they can be used to interpolate handles' 304 transformations to each bone mesh 310 vertex. The processor 610 uses the interpolated transformation at each bone mesh 310 vertex to transfer the bone mesh 310 vertex to its final location in the new anatomy 302b. In a different embodiment, the processor 610 uses Bi-Harmonic Shape Deformation (see, e.g., Yu Wang, Alec Jacobson, Jernej Barbiĕ, Ladislav Kavan: Linear Subspace Design for Real-Time Shape Deformation, ACM Transactions on Graphics 34(4) (SIGGRAPH 2015), Los Angeles, Calif., USA, ["Wang"] the entirety of which is hereby incorporated by reference herein). In this embodiment, the bone handles 304 serve as handles as defined in Wang. The bi-harmonic solve as described in Wang is then used to determine the position of any bone mesh 310 vertex. Relative to using BBWs, when applying Bi-Harmonic Shape Deformation the processor 610 does not need to perform nonlinear optimization on the bone meshes 310 to determine the BBWs. This results in faster and more robust computation.

By performing the bone mesh 310 transfer in this way, the processor 610 preserves relative proportions of the bones and joint structures from the template to the new anatomy. FIG. 3C depicts an example embodiment of the new anatomy 302h in which the bone meshes 310 are transferred by first transferring the bone handles 304, and by then transferring bone geometry using bi-harmonic shape editing as described above.

In a different embodiment, the processor 610 imposes the condition that the linear matrix F at each handle 304 has a uniform scale, by replacing F with (Trace(F)*Identity/3) (where Identity refers to the 3×3 identity matrix). This restricts linear transformations to consist of displacements and uniform scales and consequently removes rotations and shears, which improves the preservation of the shapes of the bones.

The space of allowed bone transformations may vary with the embodiment. For example, the space of allowed bone transformations may comprise any one or more of positional displacements, rotations, scaling (isotropic or otherwise) along one or both of the bone's longitudinal and transverse axes, and a scalar to control shrinking/enlarging of bone heads.

Transfer Muscles

After transferring the bone meshes 310, the processor 610 proceeds to transfer the muscle meshes 308 from the template anatomy 302a to the new anatomy 302b (block 214).

After the bone meshes 310 have been transferred, the processor 610 performs another volume interpolation of the volume enclosed by the template anatomy's 302a skin mesh 312. This time, the displacements are not specified just at the skin mesh 312, but also on the bone geometry (whose displacements the processor 610 determines when transferring the bone meshes 310). In a separate embodiment, they are also additionally specified on the fascia mesh 306. The processor 610 uses the resulting volume interpolation to transfer the template's anatomy's 302a muscle meshes 308 on to the new anatomy 302b, obtaining "geometric muscles".

To refine the result, the processor 610 optionally performs a FEM simulation of the template anatomy 302a whereby the template anatomy's 302a bone meshes 310 are linearly interpolated in a few simulation steps to the new anatomy's 302b bone meshes 310, and the FEM solver determines the corresponding muscle positions. During this FEM simulation, the simulated muscles are pushed (goaled) to the geometric muscles using a force proportional to the difference in positions between the current muscle geometry and the geometric muscle. This guides the muscles towards the geometric muscles, but at the same time smoothens and regularizes the muscle geometry due to the presence of FEM elastic energy.

The processor 610 then makes a tet mesh out of the volume between the new anatomy's 302a fascia mesh 306 and the new anatomy's 302a skin mesh 312, and treats it as fat. This may be done at a different point during anatomy transfer, such as immediately after transfer of the fascia mesh 306.

The processor does not change the template anatomy's 302a bodybuilding constants or fat proportions during anatomy transfer. In one example embodiment, the processor 610 treats the bone and muscle meshes 310,308 identically when transferring them to the new anatomy 302b and concurrently transfers them to the new anatomy 302b. Doing so may result in suboptimal bone geometry (e.g., crooked bones), but may still produce useful transferred anatomy.

Following transfer of the muscle meshes 308, an initial version of the new anatomy 302b is generated (block 216). As discussed below, this initial version may be refined through a process referred to herein as "anatomy adjustment". FIG. 3D depicts an example embodiment of the new anatomy 302b, with the muscle meshes 308 transferred as described above from the skin, fascia, and bone positions.

Figure 7A:
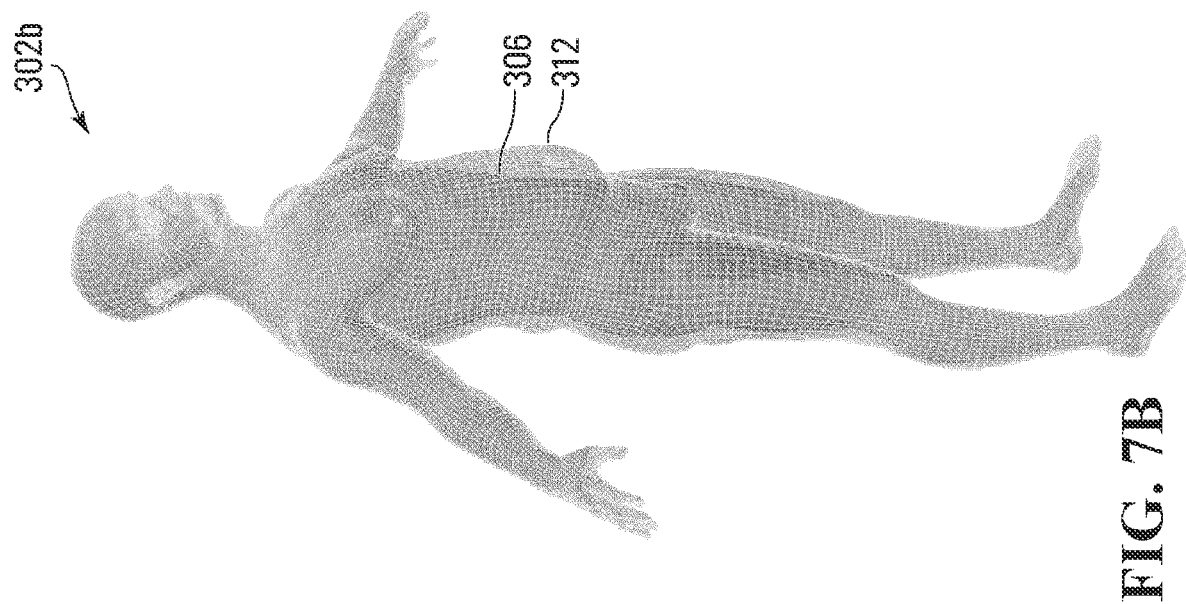
FIG. 7A depicts an example skin mesh and fascia mesh of a template anatomy.
Figure 7B:
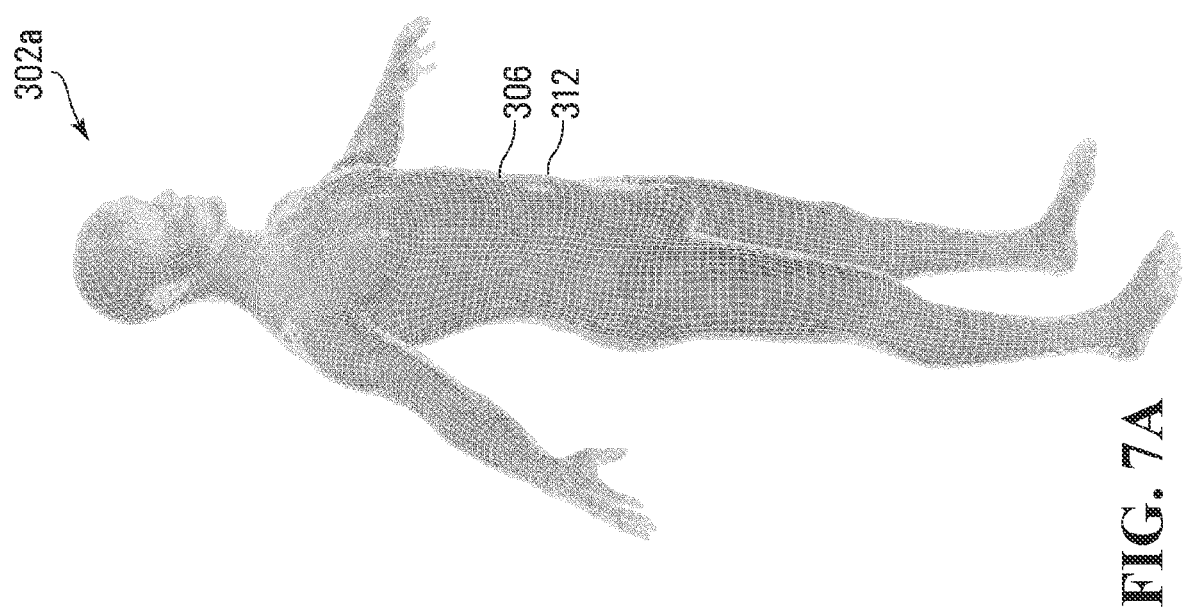
FIG. 7B depicts an example skin mesh and fascia mesh of a new anatomy that has more fat than the template anatomy of FIG. 7A.

Referring now to FIGS. 7A-7D, there are depicted an example template anatomy 302a and new anatomy 302b demonstrating application of one example of the anatomy transfer method described above. FIG. 7A depicts the skin mesh 312 and fascia mesh 306 of the template anatomy 302a, while FIG. 7B depicts the skin mesh 312 and fascia mesh 306 of the new anatomy 302b. In FIG. 7B, the skin mesh 312 is obtained using, for example, a scanner such as the depth camera 622. The fascia mesh 306 is generated by transferring the fascia mesh 306 of the template anatomy 302a to the new anatomy 302b, and by then manually adjusting a fat displacement vector for each vertex of the new anatomy's 302b skin mesh 312 to increase the amount of fat on the new anatomy 302b. The new anatomy 302b of FIG. 7B accordingly represents a fatter person than the template anatomy 302a of FIG. 7A.

Figure 7D:
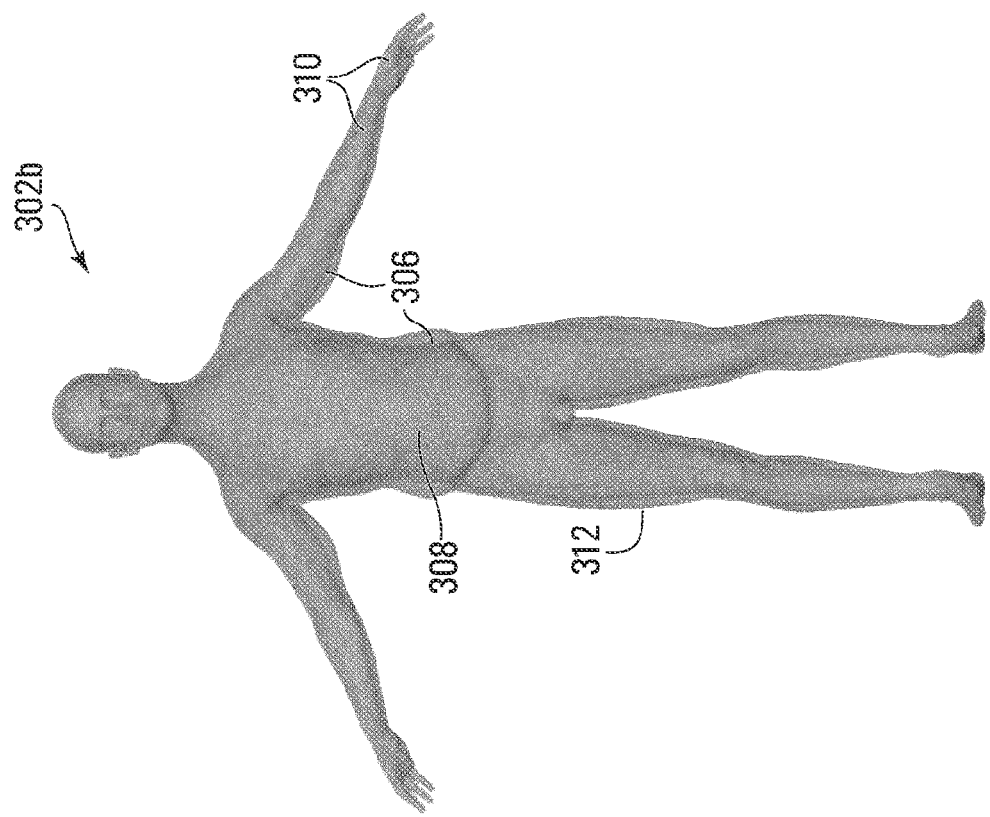
FIG. 7D depicts the new anatomy of FIG. 7B with muscle and bone meshes generated by transferring the template anatomy of FIG. 7C.
Figure 7C:
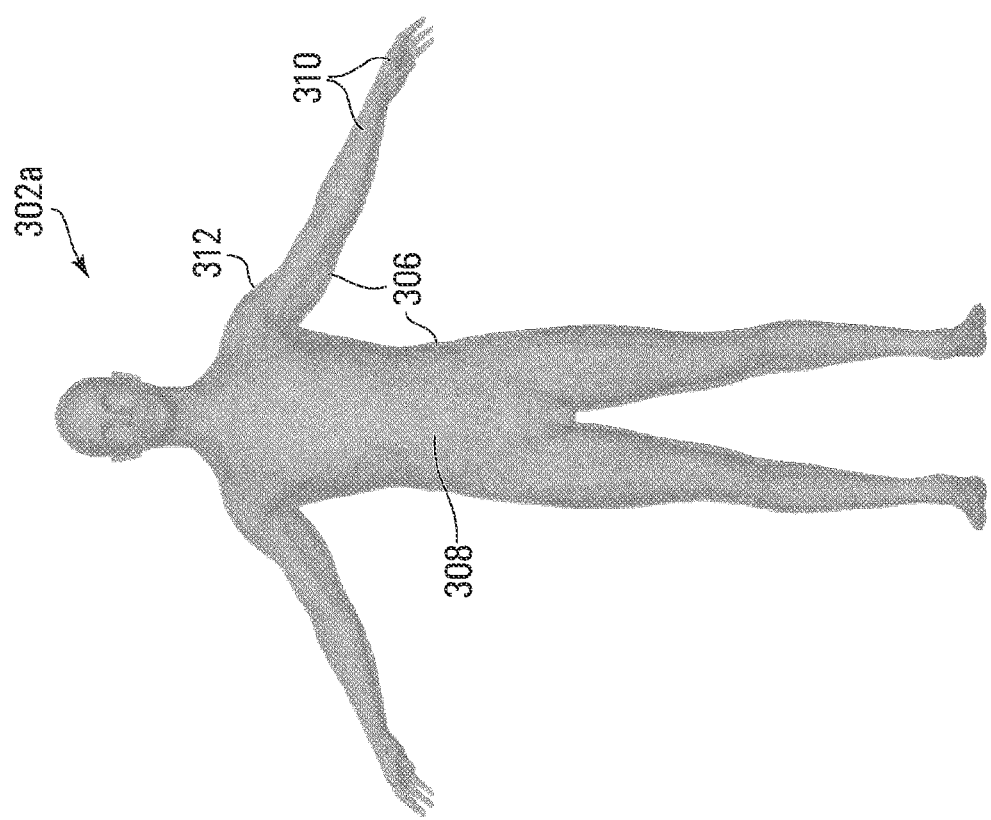
FIG. 7C depicts the template anatomy of FIG. 7A with muscle and bone meshes.

FIGS. 7C and 7D depict the template anatomy 302a of FIG. 7A and the new anatomy 302b of FIG. 7B, respectively, each complete with the muscle meshes 308 and bone meshes 310. The meshes 308,310 of the template anatomy 302a are generated using, for example, a 3D internal scan as described above. The meshes 308,310 of the new anatomy 302b are generated by applying the anatomy transfer method above to transfer the muscle and bone meshes 308,310 to the new anatomy 302b as depicted in FIG. 7B.

This manual fat displacement vector adjustment described in respect of FIG. 7B may be done immediately after the fascia mesh 306 is transferred; alternatively, the entire template anatomy 302a including the muscle and bone meshes 308,310 may be transferred a first time, following which the new anatomy's 302b fascia mesh 306 may be manually adjusted and the muscle and bone meshes 308,310 of the template anatomy 302a may then be transferred a second time in view of that adjusted fascia mesh 306 as described in respect of FIG. 7D.

Anatomy Adjustment

A user may use the processor 610 to perform anatomy adjustment after anatomy transfer, in order to refine the new anatomy 302b. During anatomy adjustment, the new anatomy's 302b bodybuilding constants and fat distributions are adjusted. Anatomy adjustment can be performed on any anatomy 302, independently of the template anatomy 302a.

The new anatomy's 302b skin mesh 312 stays constant during anatomy adjustment. Consequently, adjusting the bodybuilding constants changes the fascia mesh 306 and the processor 610 consequently changes the fat distribution (blocks 218 and 216). Similarly, if fat distribution is changed, the processor 610 consequently changes the fascia mesh 306 (blocks 220 and 216). Muscle and fat adjustments may accordingly be performed iteratively, such as by alternating between blocks 216 and 218 and blocks 216 and 220. A user may use scans, such as MRI and CT scans, images, and videos as input when deciding how to perform muscle and fat adjustments (block 222). In another embodiment (not depicted), one or both of bone and muscle adjustments may be made in response to fat adjustments, and analogously fat adjustments may be made in response to adjustments to one or both of bone and fat.

Bodybuilding Constant Adjustment

The processor 610 permits the user to control the bodybuilding constants independently for each muscle mesh 308, for each muscle group comprising multiple muscle meshes 308, or globally for all muscle meshes 308, as described in Saito. As noted above, changing the bodybuilding constant $\beta$ of a muscle enlarges ($\beta>1$) or shrinks ($\beta<1$) the muscles in a direction transverse to that which the muscle mesh 308 extends and contracts. The processor 610 determines the new muscle shape by using TEM plastic deformations as given in Saito. Specifically, for each tetrahedron of a tet mesh of the muscle mesh 308, the processor 610 determines a modified rest strain, such that the longitudinal component is 1.0, but the transverse components are modified to the bodybuilding constant $\beta$.

After the processor 610 adjusts the muscle shapes, it regenerates the fascia mesh 306. The processor 610 defines each of the muscles in the new anatomy 302b using its own tet mesh. In one embodiment, the processor 610 regenerates the fascia mesh 306 by embedding each vertex of the fascia mesh 306 into the tet mesh of a properly selected muscle, such as the geometrically nearest muscle. In a different embodiment, the processor 610 generates a tet mesh covering the template anatomy's 302a original muscle meshes 308, bone meshes 310, and fascia mesh 306. The processor 610 then determines displacement vectors of the muscle meshes' 308 vertices between the template anatomy's 302a muscle meshes 308 and the new anatomy's 302b bodybuilt positions. The processor 610 determines the minimum elastic energy configuration of the tet mesh, subject to those displacement vectors of the muscle meshes' 308 vertices. This is done by solving an optimization problem where the objective function is the tet mesh elastic energy, with the constraints being the prescribed muscle vertex displacements, and the unknown being the tet mesh vertex positions. The processor 610 then deforms the fascia mesh 306 using the resulting tet mesh deformation, resulting in the new anatomy's 302b fascia mesh 306.

After the processor 610 has regenerated the fascia mesh 306, it re-determines the fat distribution as the difference between the regenerated fascia mesh 306 and the skin mesh 312.

Fat Adjustment

A user may directly adjust fat distribution by directly adjusting the fascia mesh 306 using suitable mesh manipulation methods. The processor 610 ensures the fascia mesh's 306 topology remains constant during manipulation; alternatively, the mesh's 306 topology may change, with the processor 610 determining mesh correspondence of the unadjusted and adjusted meshes 306. After the fascia mesh 306 has been adjusted, in one embodiment the bone transfer is re-run using the skin mesh 312 and the adjusted fascia mesh 306, producing modified bone geometry. Then, the muscle transfer is re-run using the skin mesh 312, the modified bone meshes 310, and the modified fascia mesh 306, producing modified muscle meshes 308.

The new anatomy's 302b skin mesh 312 is the same after transfer and adjustment as it is before transfer and adjustment.

Transfer of Simulation-Readiness

After the anatomy transfer is complete, the new anatomy's 302b skin mesh 312, fascia mesh 306, bone meshes 310, and muscle meshes 308 are in correspondence with the template anatomy's 302a skin mesh 312, fascia mesh 306, bone meshes 310, and muscle meshes 308, respectively. The processor 610 transfers the anatomical rig of the template anatomy 302a to the new anatomy 302b as follows. For attachments between muscle meshes 308 and muscle and bone meshes 308,310, the processor 610 transfers the attachment stiffness maps from the template anatomy's 302a geometry, to the new anatomy's 302b geometry, in accordance with the correspondence. For example, if in the template anatomy 302a a muscle mesh 308 vertex is attached to a bone mesh 310 vertex with a spring of stiffness k, then in the new anatomy 302b, the corresponding muscle mesh 308 vertex is attached to the corresponding bone mesh 310 vertex also with a spring of stiffness k, respectively. If attachments are modeled using hard (exact) constraints between template anatomy 302a vertices, then the corresponding vertices in the new anatomy 302b are constrained using hard constraints. Other simulation-ready datastructures, such as, for example, collision stiffnesses, muscle fiber strengths, and simulation-mesh meshing parameters, are transferred analogously. Transfer of the anatomical rig to the new anatomy 302b may be done when the new anatomy 302b is available; for example, it may be done between anatomy transfer and adjustment or after anatomy adjustment.

Parameterization

Following anatomy transfer and adjustment, the processor 610 parameterizes the new anatomy 302b with a set of parameters that the processor 610 uses to compare different anatomies 302 to each other to assess their similarity. In one embodiment, the processor 610 may, for example, use approximately 20 parameters per anatomy 302; this number may vary in different embodiments depending on the required accuracy. The processor 610 separately parameterizes the exterior (i.e., skin mesh 312) of the new anatomy 302b and the interior of the new anatomy 302b, as discussed in further detail below.

Principal Components Analysis ("PCA") is used for parameterization. PCA is a technique used in computer animation and data processing, as follows. Let $x_1, \ldots, x_N$ be a dataset of n-dimensional vectors, consisting of N vectors (e.g., N>100). Then, the center vector is first formed as $$\bar{x} = \frac{1}{N} \sum_{i=1}^{N} x_1.$$

Singular value decomposition is then performed on the matrix $[x_1-\bar{x}, \ldots, x_N-\bar{x}]=U\Sigma V^T$. The first r columns (e.g., r=20) of U are called the principal eigenvectors. They represent the first r most important variabilities found in the dataset $x_1, \ldots, x_N$. An arbitrary vector x can then be parameterized with r parameters as $U^T x$.

The processor 610 parameterizes the skin mesh 312 using eigenvectors as described in Brett Allen, Brian Curless, Zoran Popovic: The space of human body shapes: reconstruction and parameterization from range scans, ACM SIGGRAPH 2003, the entirety of which is hereby incorporated by reference herein ("Allen"). As explained by Allen, this is done by performing PCA on a dataset of skin mesh 312 vertex positions; the dataset may comprise a database 118 (depicted in FIG. 1) of additional anatomies 302 generated based on the template anatomy 302a. The vectors $x_1, \ldots, x_N$ correspond to N anatomies 302 which, in the present example embodiment, model humans. The skin meshes 312 for the N anatomies 302 have the same topology, but different vertex positions to account for variability in a typical human population. Each vector gives the positions of all vertices in the mesh 312 for one specific human. The principal eigenvectors, referred to interchangeably herein as "eigenbodies", are the dominant variations of the body shape away from the average body shape of anatomies in the database 118. While humans form the basis of the present example embodiment, in different embodiments the anatomies 302 may model creatures such as cats, dogs, dragons, and elephants.

In contrast to Allen, the processor 610 also parameterizes the interior of the new anatomy 310b using the new anatomy's 310b fat distribution, projected to a low-dimension space, thereby forming eigenvectors parameterizing the new anatomy 310b and the additional anatomies 302 in the database 118; these fat eigenvectors are hereinafter interchangeably referred to as "eigenfats". The processor 610 generates the "eigenfat" principal vectors by performing PCA on the fat displacement fields of the anatomies 302 in the database 118, which in the present example comprises the new anatomy 302b. The processor 302b retains a number (e.g., 20) of the first "eigenfats", which are most responsible for the variances within the dataset, and uses them to parameterize the fat distribution. Given any new fat displacement field f, its parameter is calculated as $U^T_f$, where U is the matrix of "eigenfat" principal vectors obtained from PC A.

In a different embodiment, the processor 610 also normalizes the "eigenfat" parameterization to take into account the external shape variability of the anatomies 302 in the database 118. This normalizes for the fact that a larger person has more fat than a smaller person, even if both are considered equally overweight, i.e., the eigenfats are made independent of the geometric proportions of the subject forming the basis of the anatomy 302. This is achieved by transferring the fascia mesh 306 of each anatomy 302 in the database back to the template anatomy 302a. The skin mesh 312 of each anatomy 302 in the database 118 is used as a starting point and transferred to the template anatomy's 302a skin mesh 312. The processor 610 then determines the displacement fields between the fascia mesh 306 after it has been transferred and the skin mesh 312 of the template anatomy 302a, forming "normalized fat displacement fields". The processor 610 then applies the eigenfat procedure as described above and performs parameterization with respect to those normalized fat displacement fields. Consequently, the effects of different anatomies 302 in the database 118 being taller, heavier, etc., than each other are mitigated when performing parameterization.

The processor 610 stores the final parameterization of each new anatomy 302b as a concatenation of the external and internal parameters.

Growth of the Database of Simulation-Ready Anatomies

The anatomy transfer and parameterization described above can be employed to generate and grow a large database 118 of simulation-ready anatomies. In one example embodiment, the processor 610 generates and parameterizes multiple new anatomies 302b using the template anatomy 302a and multiple exterior scans of different individuals as described above. The processor 610 then automatically determines whether to add each of the new anatomies 302a to a database 118 of simulation-ready anatomies as follows.

If the database 118 is empty, the processor 610 adds the first anatomy 302 it considers to the database. The first anatomy 302 may be the template anatomy 302a or any one of the new anatomies 302b.

When the database 118 is not empty, in one embodiment the processor 610 determines whether to add one of the new anatomies 302b to the database 118 based on the external parameters (i.e., "eigenbodies") of the new anatomy 302b and the external parameters of the anatomies 302 already in the database 118. The processor 610 compares the external parameters of the new anatomy 302b to the external parameters of each of the anatomies 302 stored in the database 118.

The processor 610 determines whether the external parameters of the new anatomy 302b are sufficiently far from the external parameters of each of the anatomies 302 stored in the database 118 by determining whether the distances between the parameters of the two anatomies 302b,302 satisfies an external parameter difference threshold. The distance between two parameters p and q may be any suitable distance measure between vectors in mathematics, for example, the $L_2$ distance (square root of the sum of squared vector entry differences), $\sqrt{\Sigma_{i=1}^{r}(p_i-q_i)^2}$. When the processor 610 determines that the external parameter difference is satisfied, the processor 610 adds the new anatomy 302b to the database 118. When this difference is not satisfied, the processor 610 determines that the new anatomy 302b is too similar to at least one of the anatomies 302 already in the database 118 and consequently does not add the new anatomy 302b to the database 118. Comparing only external parameters saves computational time, as the processor 610 does not need to transfer or compare interiors of the anatomies 302,302b.

In another embodiment, when the database 118 is not empty the processor 610 determines whether to add one of the new anatomies 302b to the database 118 based on the interior (i.e., "eigenfats") and external parameters. The processor 610 determines whether the internal and external parameters of the new anatomy 302b are sufficiently far from the internal and external parameters of each of the anatomies 302 stored in the database 118 by determining whether the distances between the parameters of the two anatomies 302b,302 satisfies a combined parameter difference threshold. Again, the distance measure between two vectors can be any suitable distance measure, for example, the $L_2$ distance. The internal and external parameters in certain embodiments may be weighted relative to each other, using a user-adjustable weight, to emphasize the relative importance of external vs. internal parameters. When the processor 610 determines that the combined parameter difference is satisfied, the processor 610 adds the new anatomy 302b to the database 118. When this difference is not satisfied, the processor 610 determines that the new anatomy 302b is too similar to at least one of the anatomies 302 already in the database 118, and consequently does not add the new anatomy 302b to the database 118. Comparing internal and external parameters better covers the space of all individuals modeled by the anatomies 302, as it is possible to store in the database anatomies 302 having similar exteriors but sufficiently different interiors, at the cost of computational resources.

Figure 1:
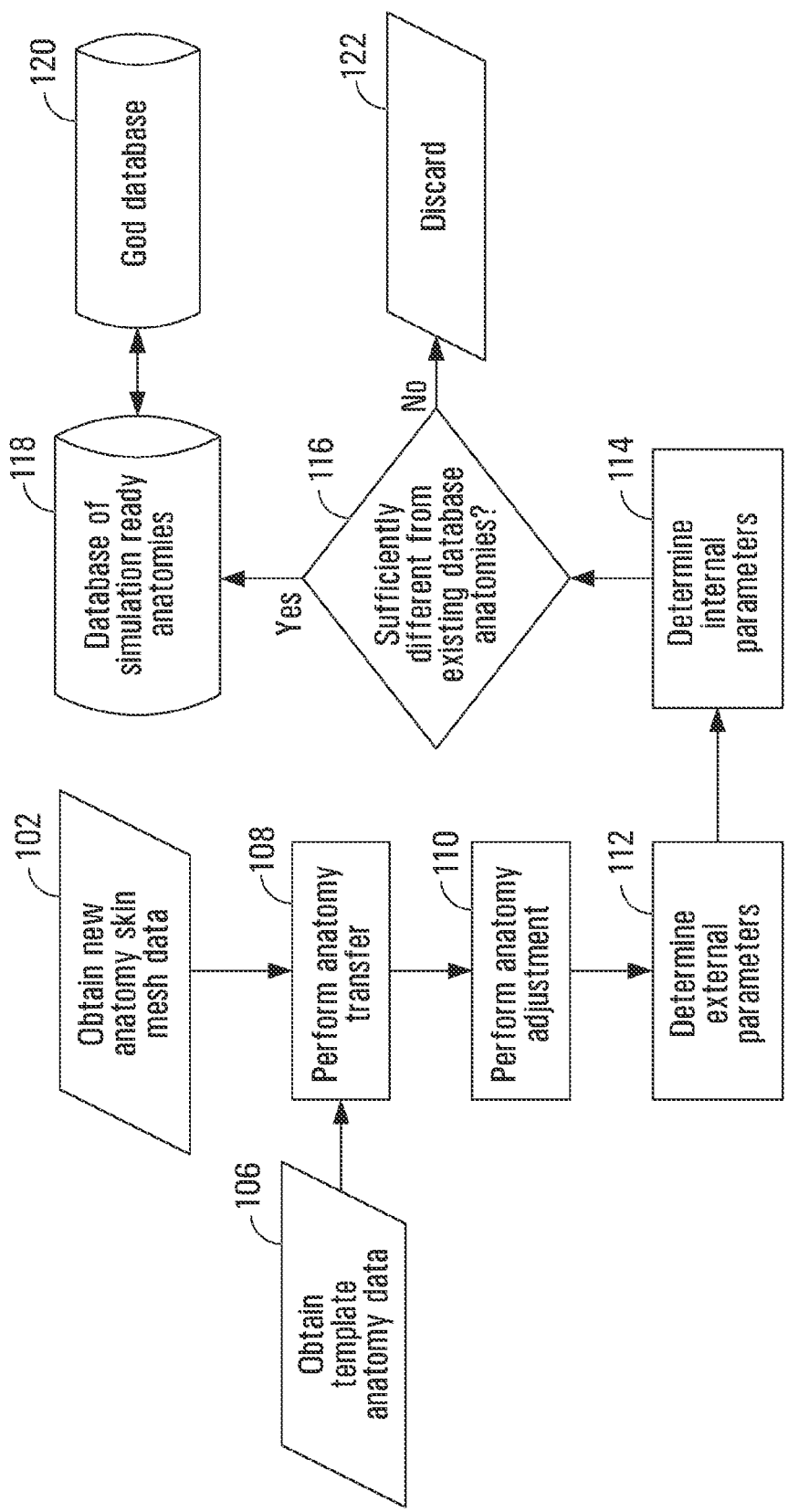
FIGS. 1 and 2 depict flow diagrams for generating an anatomy, according to example embodiments.

FIG. 1 shows an overview of the anatomy transfer and anatomy adjustment processes described above. At block 102, the processor 610 obtains the skin mesh 312 of the new anatomy 302b, such as via an external scan of an individual for whom the new anatomy 302b is to be personalized. At block 106, the processor 610 obtains the template anatomy 302b, with the template anatomy 302b in the depicted embodiment comprising a skin mesh 312, fascia mesh 306, bone meshes 310, muscle meshes 308, and an anatomical rig. The processor 610 then performs anatomy transfer at block 108 and subsequently performs anatomy adjustment at block 110, as shown in more detail in respect of FIG. 2. The new anatomy 302b is created after anatomy adjustment is completed.

After the new anatomy 302b is created, the processor 610 determines its external and internal parameters at blocks 112 and 114 with reference to other anatomies 302 already present in the database 118. In the depicted embodiment, all the anatomies 302 in the database 118 were generated using the same template 302a and accordingly their respective skin, fascia, muscle, and bone meshes 312,306,308,310 are all automatically in correspondence with each other. In a different embodiment, the anatomies 302 in the database 118 may not be generated based on the template anatomy 302a and instead may first be put into correspondence with each other by having the processor 610 perform mesh registration on them.

After parameterization, the processor 610 at block 116 compares the parameters of the new anatomy 302a to the parameters of the anatomies 302 already in the database 118 to determine whether the new anatomy 302b is sufficiently different from those database anatomies 302 to be added to the database 118. If not, the new anatomy 302b is discarded (block 122). If the processor 610 determines there is sufficient difference, the new anatomy 302b is added to the database 118. All anatomies 302 ever added to the database 118 in FIG. 1 are also backed up in a "God database" 120 for reference.

Regression

Even though the external and internal parameters are in principle independent of each other, there is in practice a certain degree of correlation between them. The processor 610 in certain embodiments accordingly may perform regression to predict the internal parameters from the external parameters. For example, given a database 118 of N anatomies 302, each possessing one or more exterior and internal parameters, the processor 610 may perform a regression by building a linear regression model $p_{internal}=A p_{external}+b$, where A is a suitable matrix, and b is a suitable vector. The processor determines them by minimizing a least-square problem, $$\min_{A,b} \sum_{i=1}^{N} \|(p^i_{internal} - (A p^i_{external} + b))\|^2.$$

In different embodiments, the processor 610 may use a non-linear regression.

Interpolation to Novel Anatomies

In certain embodiments, the processor 610 interpolates one or more new anatomies 302b given the anatomies 302 present in the database 118. In certain of these embodiments, the processor 610 uses a parameter $p=(p_{external}, p_{internal})$ for interpolation. FIGS. 5A-5D depict flow diagrams for generating an anatomy using interpolation, according to additional example embodiments.

Figures 5A, 5B:
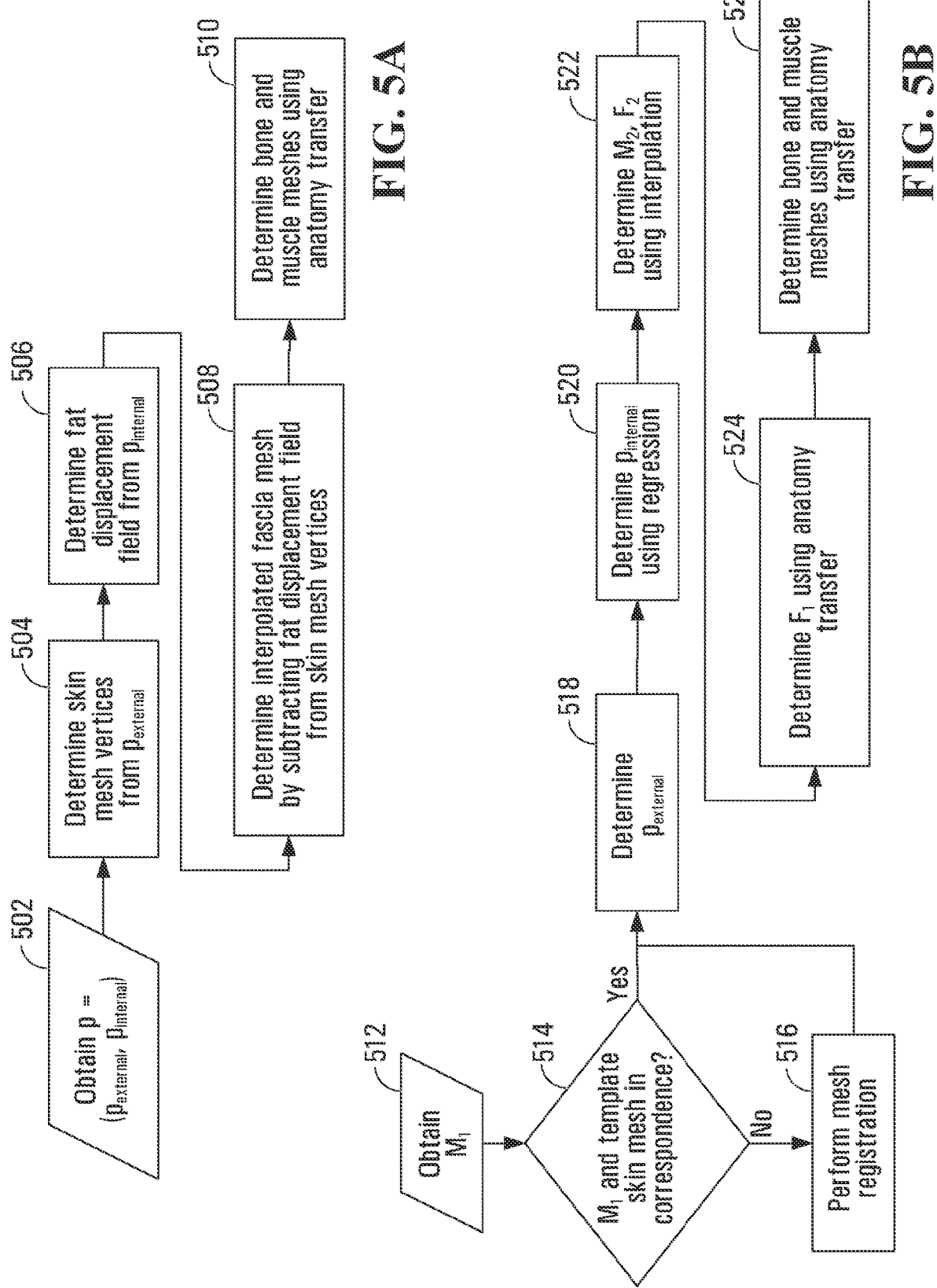
FIGS. 5A-5D depict flow diagrams for generating an anatomy using interpolation, according to additional example embodiments.

In one example embodiment ("first interpolation embodiment") as shown in FIG. 5A, the processor 610 determines the skin mesh 312 and fascia mesh 306 based on p, automatically and without any manual intervention, as follows. The processor 610 first obtains p (block 502). In this example, the specific method of obtaining p is irrelevant; it may, for example, be determined as described below for the other embodiments of interpolation or may be determined using a different method. In this embodiment, the processor 610 sets the positions of the vertices of the skin mesh 312 to $\bar{x}_{skin}+U_{skin} p_{external}$ (block 504), where $\bar{x}_{skin}$ and $U_{skin}$ are determined using PCA as described above and the "skin" subscript denotes quantities referring to the skin mesh 312 (e.g., $U_{skin}$ represents "eigenbodies"); $\bar{x}_{skin}$ may more generally be any suitable external starting vector for use in interpolation. The fat displacement field is set to $\bar{x}_{fat}+U_{fat} p_{internal}$ (block 506), where $\bar{x}_{fat}$ and $U_{fat}$ are again determined using PCA as described above and the "fat" subscripts denotes quantities referring to fat (e.g., $U_{fat}$ represents "eigenfats"); $\bar{x}_{fat}$ may more generally be any suitable internal starting vector for use in interpolation. The processor 610 then determines the fascia mesh 306 of the new anatomy 302b by subtracting the fat displacement field $(\bar{x}_{fat}+U_{fat} p_{internal})$ from the vertices of the skin mesh 312 $(\bar{x}_{skin}+U_{skin} p_{external})$ (block 508). In an embodiment in which the fat has been normalized with respect to body shape as described above, the processor 610 performs interpolation using the normalized fascia meshes 306 in the database 118, resulting in the interpolated normalized fascia meshes 306. The actual fascia mesh 306 for the new anatomy 302b is then obtained by performing anatomy transfer, between the template anatomy's 302a skin mesh 312 and the new anatomy's 302b skin mesh 312, of the interpolated normalized fascia mesh 306.

Once the processor 610 determines the skin and fascia meshes 312,306 for the new anatomy 302b through interpolation, the processor 610 automatically transfers the template anatomy's 302a bone and muscle meshes 310,308 to the new anatomy 302b, as described above in respect of anatomy transfer (block 510).

In another embodiment ("second interpolation embodiment") as shown in FIG. 5B, the new anatomy 302b is already defined by its skin mesh 312, referred to in this embodiment as "$M_1$". The processor 610 obtains $M_1$ (block 512) and determines whether it has the same topology as the template anatomy's 302a skin mesh 312, or has otherwise been brought into correspondence with the template anatomy's 302a skin mesh 312 (block 514). If not, the processor 610 performs mesh registration to bring $M_1$ and the template anatomy's 302a skin mesh 312 into correspondence (block 516). Once the meshes are in correspondence, the processor 610 generates $p_{external}=U_{skin}^T x$ (block 518), where x are the vertices of $M_1$. The processor 610 then uses regression as described above to determine $p_{internal}$ (block 520). The processor 610 then performs the interpolation as described in the first interpolation embodiment described above, producing the interpolated skin mesh 312 ("$M_2$" in this embodiment) and interpolated fascia mesh 306 ("$F_2$" in this embodiment) (block 522). The positions of the vertices of $M_2$ corresponding to parameter p are $\bar{x}_{skin}+U_{skin} U_{skin}^T x$, which are near but not necessarily equal to $M_1$, which is the desired skin mesh 312. The processor 610 remedies this by performing a fascia mesh 306 transfer as described above in respect of anatomy transfer (block 524), where the source skin and fascia meshes 312,306 are $M_2$, $F_2$, and the target skin mesh is $M_1$. This produces the new anatomy's fascia mesh 306 ("$F_1$" in this embodiment). The bone and muscle meshes 310,308 are then transferred to the new anatomy 302b as described above in respect of anatomy transfer (block 526).

Figure 5C:
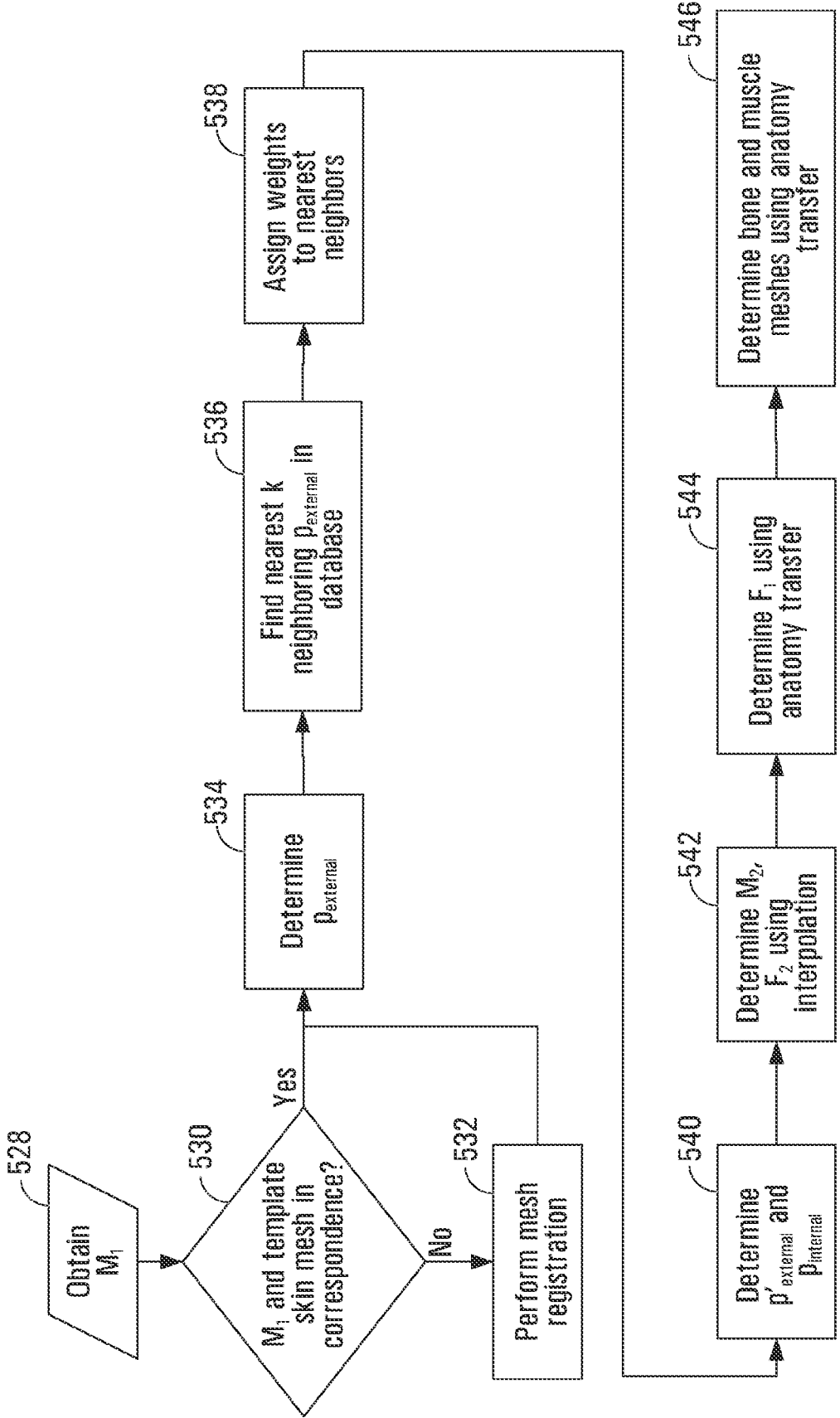

In another example embodiment ("third interpolation embodiment") as shown in FIG. 5C, the new anatomy 302b is already defined by its skin mesh 312, referred to in this embodiment as "$M_1$". As before, the processor 610 obtains $M_1$ (block 528) and determines whether it has the same topology as the template anatomy's 302a skin mesh 312, or has otherwise been brought into correspondence with the template anatomy's 302a skin mesh 312 (block 530). If not, the processor 610 performs mesh registration to bring $M_1$ and the template anatomy's 302a skin mesh 312 into correspondence (block 532). The processor 610 generates $p_{external}=U_{skin}^T x$ (block 534), where x are the vertices of $M_1$. The processor 610 then finds the nearest k neighboring external parameters in the database 118 to $p_{external}$ (e.g., k=4) (block 536). The processor 610 determines the distance $p_{external}$ of $M_1$ and $p_{external}$ of each of the anatomies 302 in the database 118 using any of the standard distance measures between vectors, for example, the $L_2$ distance. The processor 610 then assigns weights $w_1, \ldots, w_k$ to each of those nearest neighbors (block 538). For example, one suitable assignment of weights is to impose that they sum to 1.0, and make $w_1$ inversely proportional to the distance between $p_{external}$ and the $i^{th}$ nearest neighbor, for example, by using Shepard's weights (see, e.g., Shepard, Donald: A two-dimensional interpolation function for irregularly-spaced data. Proceedings of the 1968 ACM National Conference. pp. 517-524, the entirety of which is hereby incorporated by reference herein). The processor 610 then determines a new external parameter, $p'_{external} = \Sigma_{i=1}^{k} w_i p^i_{external}$, where $p^i_{external}$ is the $i^{th}$ nearest neighbor to $p_{external}$ (block 540). The processor 610 also determines the internal parameter $p_{internal} = \Sigma_{i=1}^{k} w_i p^i_{internal}$, where $p^i_{internal}$ is the internal parameter stored in the database 118 at the $i^{th}$ nearest neighbor (block 540). The processor 610 then proceeds as explained in the second interpolation embodiment, with the input $p=(p'_{external}, p_{internal})$, producing the interpolated skin mesh 312 $M_2$ and interpolated fascia mesh 306 $F_2$ (block 542). As in the second interpolation embodiment, the positions of the vertices of the interpolated skin mesh 312 $M_2$ are not necessarily equal to the actual desired skin mesh 312 $M_1$. The processor 610 remedies this by performing an automatic anatomy transfer of the fascia mesh 306, as described in respect of anatomy transfer, where the source skin and fascia meshes 312, 306 are $M_2$, $F_2$, and the target skin mesh is $M_1$ (block 544). This produces the new anatomy's fascia mesh 306 ("$F_1$" in this embodiment). The bone and muscle meshes 310, 308 are then transferred to the new anatomy 302b as described above in respect of anatomy transfer (block 546). Similar to the second interpolation embodiment, this embodiment has good extrapolation properties Because the parameters are low-dimensional, this embodiment has the advantage that the nearest neighbor search can be performed faster, and is more robust, which is useful for large databases 118 of subjects.

Figure 5D:
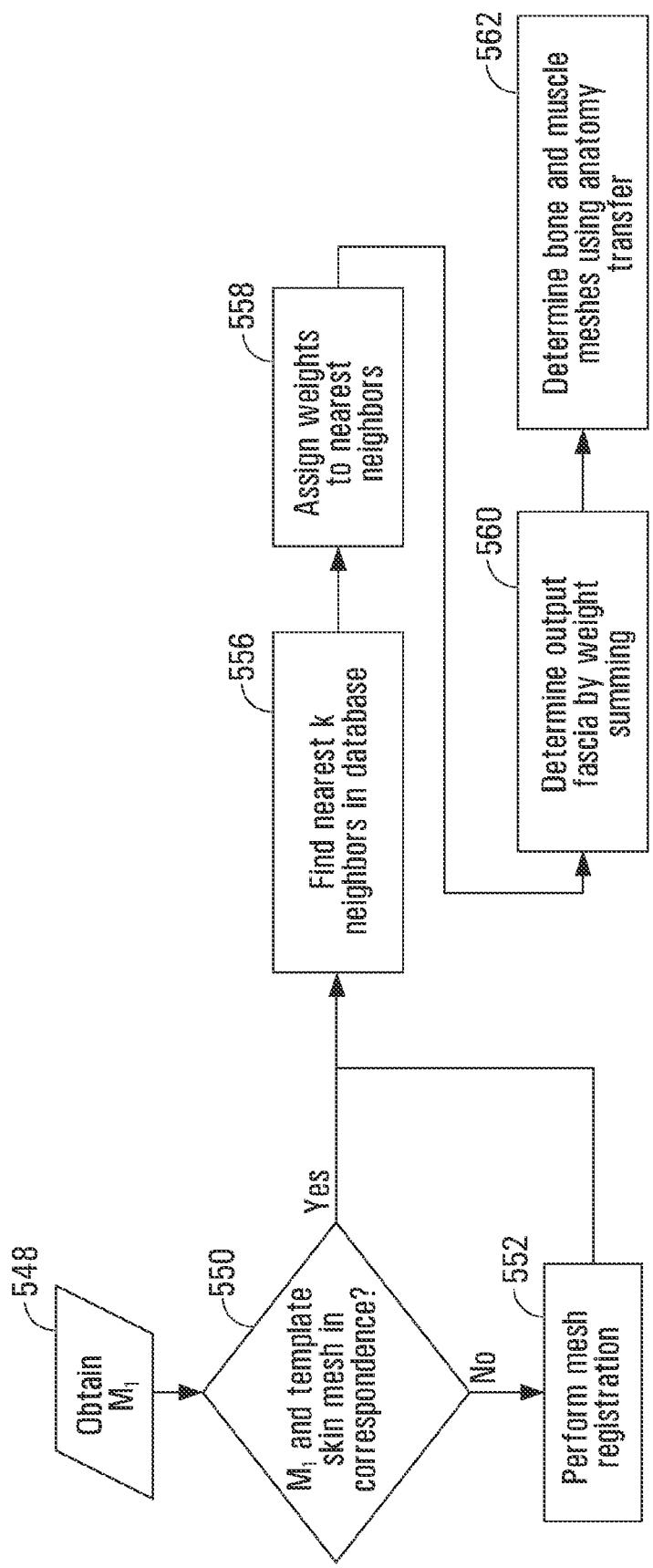

In another example interpolation embodiment ("fourth interpolation embodiment") as shown in FIG. 5D, the new anatomy 302b is already defined by its skin mesh 312, referred to in this embodiment as "$M_1$". As before, the processor 610 obtains $M_1$ (block 548) and determines whether it has the same topology as the template anatomy's 302a skin mesh 312, or has otherwise been brought into correspondence with the template anatomy's 302a skin mesh 312 (block 550) if not, the processor 610 performs mesh registration to bring $M_1$ and the template anatomy's 302a skin mesh 312 into correspondence (block 552). The processor 610 finds the nearest k neighboring skin meshes 312 in the database 118 to $M_1$ (e.g., k=4) (block 556). The processor 610 determines the distance between two meshes 312 by forming the two vectors of their vertex positions, and then determines any of the standard distance measures between vectors, for example, the $L_2$ distance. The processor 610 then assigns weights $w_1, \ldots, w_k$ to these nearest neighbors (block 558). For example, one suitable assignment of weights is to impose that they sum to 1.0, and to make $w_i$ inversely proportional to the distance between $M_1$ and the $i^{th}$ nearest neighbor, for example, by using Shepard's weights. The processor 610 then determines the output fascia mesh 306 by weight-summing the corresponding fascia meshes 306 of those nearest neighbors (block 560). If $F_1, \ldots, F_k$ are vectors representing the positions of the vertices of the fascia meshes 306 in the nearest neighbors 1, . . . , k, the output fascia mesh 306 is $\Sigma_{i=1}^{k} w_i F_i$. The bone and muscle meshes 310, 308 are then transferred to the new anatomy 302b as described above in respect of anatomy transfer (block 562). The advantages of this embodiment are that it fails gracefully when the skin mesh $M_1$ is outside of the space covered by the database, and that it does not require the fascia mesh 306 to be transferred as described above in respect of anatomy transfer.

In an alternative to the fourth interpolation embodiment, the processor 610 determines the fascia mesh 306 as in the fourth interpolation embodiment. However, it then also forms the bone and muscle meshes 310, 308 using interpolation: if $B_1, \ldots, B_k$ are the positions of the vertices of the bone meshes 310 in the nearest neighbors 1, . . . , k, the output geometry of the bone meshes 310 is $\Sigma_{i=1}^{k} w_i B_i$. The processor 610 analogously determines the geometry of the muscle meshes 308. An advantage of this alternative embodiment is that no anatomy transfer is required.

Regardless of the interpolation embodiment, after the meshes 306, 308, 310, 312 of the new anatomy 302b have been created, the processor 610 transfers the anatomical rig from the template anatomy 302a on to the new anatomy 302b determined using interpolation, as described for anatomy transfer.

Figure 2:
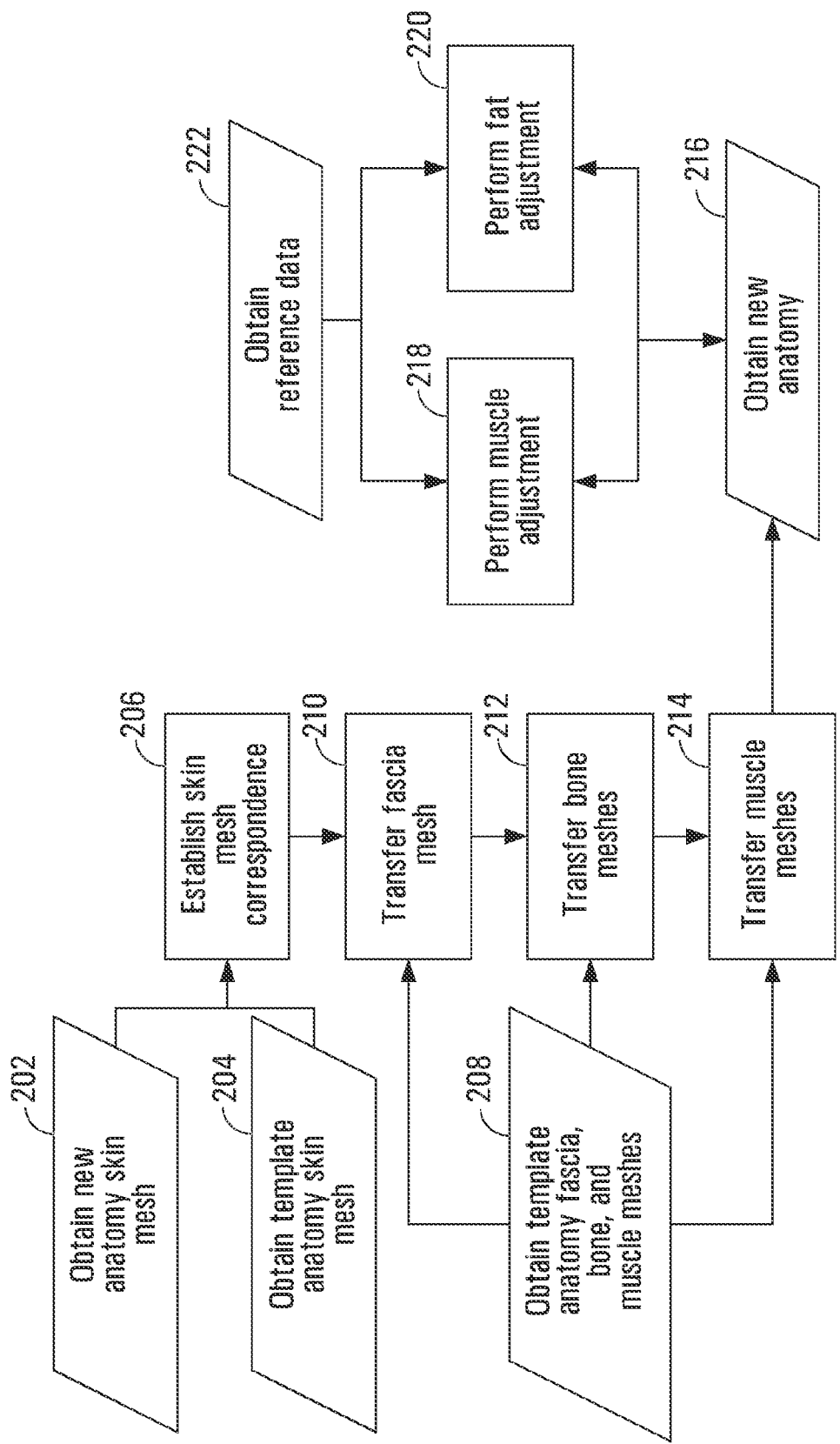

By using a diverse database of many subjects, in combination with interpolation, fat and muscle adjustment as shown in blocks 218 and 220 of FIG. 2 can be avoided, making it possible for processor 610 to generate a quality novel anatomy completely automatically. For example, if an overweight person is to be modeled using the new anatomy 302b and the template anatomy 302a is of a lean person, in the embodiment of FIG. 2 anatomy adjustment is done in order to manually adjust the transferred, template anatomy 302a to better represent the overweight person modeled by the new anatomy 302b. However, given a database 118 that already includes many overweight anatomies 302, the processor 610 in the interpolation embodiments may interpolate from those overweight anatomies 302 to generate the new anatomy 302b. In this way, manual anatomy adjustment can be avoided.

The embodiments have been described above with reference to flowcharts and block diagrams of methods, apparatuses, systems, and computer program products. In this regard, the flowcharts and block diagrams of FIGS. 1 and 2 illustrate the architecture, functionality, and operation of implementations of various embodiments. For instance, each block of the flowcharts and block diagrams may represent a module, segment, or portion of code, which comprises one or more executable instructions for implementing the specified action(s). In some alternative embodiments, the action(s) noted in that block may occur out of the order noted in those figures. For example, two blocks shown in succession may, in some embodiments, be executed substantially concurrently, or the blocks may sometimes be executed in the reverse order, depending upon the functionality involved. Some specific examples of the foregoing have been noted above but those noted examples are not necessarily the only examples. Each block of the block diagrams and flowcharts, and combinations of those blocks, may be implemented by special purpose hardware-based systems that perform the specified functions or acts, or combinations of special purpose hardware and computer instructions.

Each block of the flowcharts and block diagrams and combinations thereof can be implemented by computer program instructions. These computer program instructions may be provided to a processor of a computer, such as one particularly configured to anatomy generation or simulation, or other programmable data processing apparatus to produce a machine, such that the instructions, which execute via the processor of the computer or other programmable data processing apparatus, create means for implementing the actions specified in the blocks of the flowcharts and block diagrams.

These computer program instructions may also be stored in a computer readable medium that can direct a computer, other programmable data processing apparatus, or other devices to function in a particular manner, such that the instructions stored in the computer readable medium produce an article of manufacture including instructions that implement the actions specified in the blocks of the flowcharts and block diagrams. The computer program instructions may also be loaded onto a computer, other programmable data processing apparatus, or other devices to cause a series of operational steps to be performed on the computer, other programmable apparatus, or other devices to produce a computer implemented process such that the instructions that execute on the computer or other programmable apparatus provide processes for implementing the actions specified in the blocks of the flowcharts and block diagrams.

Figure 6:
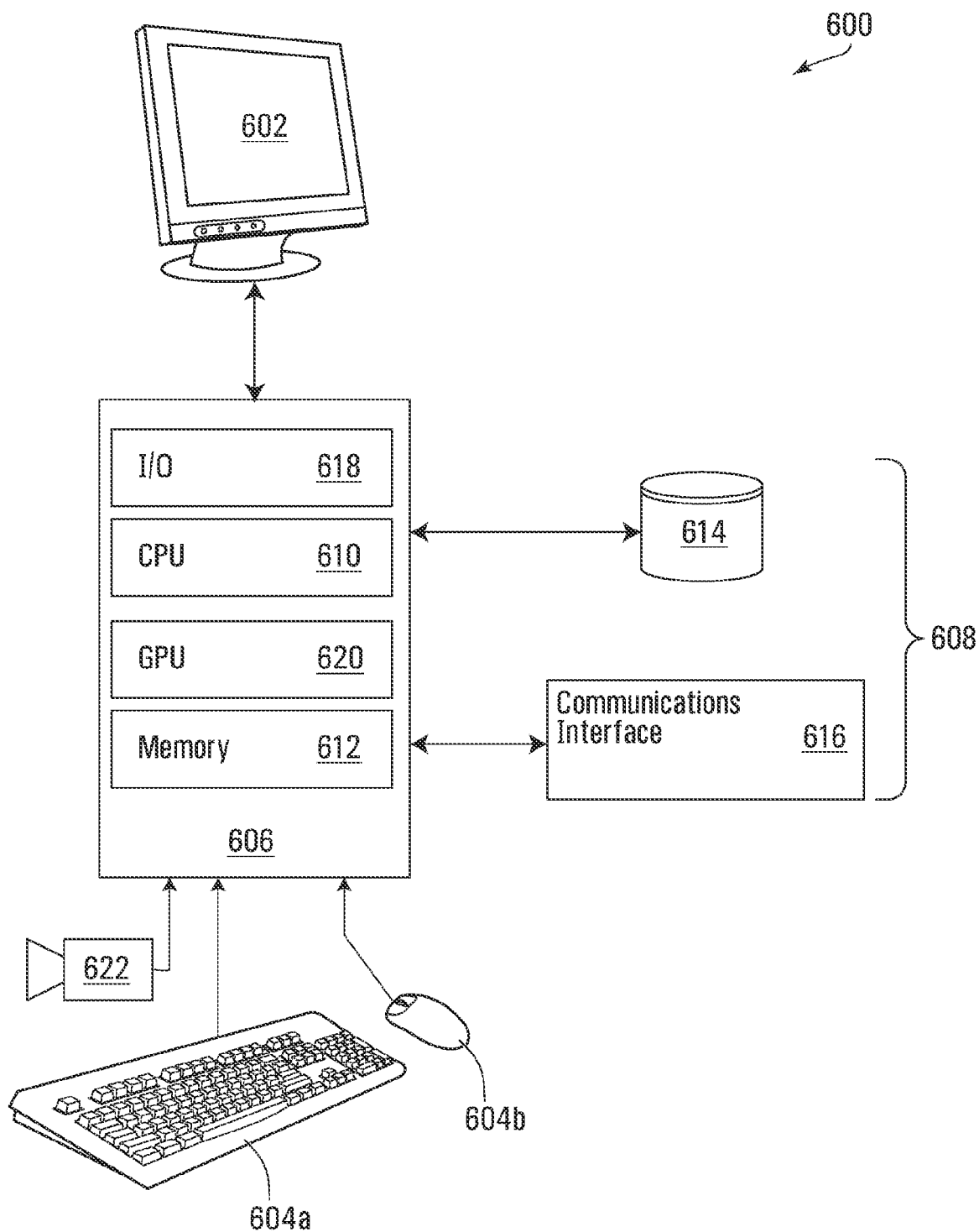
FIG. 6 depicts a system for generating an anatomy, according to another embodiment.

An illustrative computer system 600 in respect of which the methods herein described may be implemented is presented as a block diagram in FIG. 6. The computer system 600 comprises a display 602, input devices in the form of keyboard 604a, pointing device 604b, and depth camera 622; computer 606, and external devices 608. While the pointing device 604b is depicted as a mouse, other types of pointing devices may also be used. In alternative embodiments (not depicted), the computer system 600 may not comprise all the components depicted in FIG. 6.

The computer 606 may comprise one or more processors or microprocessors, such as a central processing unit (CPU) 610, which is depicted. The CPU 610 performs arithmetic calculations and control functions to execute software stored in an internal memory 612, such as one or both of random access memory (RAM) and read only memory (ROM), and possibly additional memory 614. The additional memory 614 may comprise, for example, mass memory storage, hard disk drives, optical disk drives (including CD and DVD drives), magnetic disk drives, magnetic tape drives (including LTO, DLT, DAT and DCC), flash drives, program cartridges and cartridge interfaces such as those found in video game devices, removable memory chips such as EPROM or PROM, emerging storage media, such as holographic storage, or similar storage media as known in the art. This additional memory 614 may be physically internal to the computer 606, or external as shown in FIG. 6, or both.

The computer system 600 may also comprise other similar means for allowing computer programs or other instructions to be loaded. Such means can comprise, for example, a communications interface 616 that allows software and data to be transferred between the computer system 600 and external systems and networks. Examples of the communications interface 616 comprise a modem, a network interface such as an Ethernet card, a wireless communication interface, or a serial or parallel communications port. Software and data transferred via the communications interface 616 are in the form of signals which can be electronic, acoustic, electromagnetic, optical, or other signals capable of being received by the communications interface 616. Multiple interfaces, of course, can be provided on the computer system 600.

Input to and output from the computer 606 is administered by the input/output (I/O) interface 618. The I/O interface 618 administers control of the display 602, keyboard 604a, external devices 608, depth camera 622, and other analogous components of the computer system 600. The computer 606 also comprises a graphical processing unit (GPU) 620. The GPU 620 may also be used for computational purposes as an adjunct to, or instead of, the CPU 610, for mathematical calculations. However, as mentioned above, in alternative embodiments (not depicted) the computer system 600 need not comprise all of these elements.

The various components of the computer system 600 are coupled to one another either directly or indirectly by shared coupling to one or more suitable buses.

The terminology used herein is for the purpose of describing particular embodiments only and is not intended to be limiting. Accordingly, as used herein, the singular forms "a", "an", and "the" are intended to include the plural forms as well, unless the context clearly indicates otherwise. It will be further understood that the terms "comprises" and "comprising", when used in this specification, specify the presence of one or more stated features, integers, steps, operations, elements, and components, but do not preclude the presence or addition of one or more other features, integers, steps, operations, elements, components, and groups. Directional terms such as "top", "bottom", "upwards", "downwards", "vertically", and "laterally" are used in the following description for the purpose of providing relative reference only, and are not intended to suggest any limitations on how any article is to be positioned during use, or to be mounted in an assembly or relative to an environment. Additionally, the term "couple" and variants of it such as "coupled", "couples", and "coupling" as used in this description are intended to include indirect and direct connections unless otherwise indicated. For example, if a first device is coupled to a second device, that coupling may be through a direct connection or through an indirect connection via other devices and connections. Similarly, if the first device is communicatively coupled to the second device, communication may be through a direct connection or through an indirect connection via other devices and connections.

It is contemplated that any part of any aspect or embodiment discussed in this specification can be implemented or combined with any part of any other aspect or embodiment discussed in this specification.

In construing the claims, it is to be understood that the use of computer equipment, such as a processor, to implement the embodiments described herein is essential at least where the presence or use of that computer equipment is positively recited in the claims.

One or more example embodiments have been described by way of illustration only. This description is been presented for purposes of illustration and description, but is not intended to be exhaustive or limited to the form disclosed. It will be apparent to persons skilled in the art that a number of variations and modifications can be made without departing from the scope of the claims.

The invention claimed is:

1. A non-transitory computer-readable storage medium for generating a new anatomy, the medium comprising:
   obtaining a skin mesh of the new anatomy that is in correspondence with a skin mesh of a template anatomy;
   transferring a fascia mesh of the template anatomy to the new anatomy;
   generating a fat displacement field defining fat of the new anatomy, the displacement field comprising multi-dimensional displacement vectors, each of the displacement vectors relating a vertex of the skin mesh of the new anatomy to a corresponding vertex of the fascia mesh of the new anatomy;

parameterizing the new anatomy relative to additional anatomies, a skin mesh and a fascia mesh of each of the additional anatomies in correspondence with the skin mesh and the fascia mesh of the new anatomy; and adding the new anatomy to a database based on a comparison of one or more parameters of the new anatomy with one or more parameters of the additional anatomies.

2. The non-transitory computer-readable storage medium of claim 1, wherein the parameterizing of the new anatomy comprises:

generating external parameters parameterizing an exterior of each of the new anatomy and the additional anatomies by performing principal components analysis on vertex positions of the skin meshes of the new anatomy and the additional anatomies to determine body eigenvectors for each of the new anatomy and the additional anatomies; and adding the external parameters to the database.

3. The non-transitory computer-readable storage medium of claim 1, wherein the adding the new anatomy to the database comprises:

for each of the additional anatomies, determining an exterior difference between an external parameter of the new anatomy and an external parameter of the additional anatomy and comparing the exterior difference to an external parameter difference threshold; and adding the new anatomy to the database based on the external parameter difference threshold being satisfied for one or more of the additional anatomies.

4. The non-transitory computer-readable storage medium of claim 1, wherein each of the additional anatomies further comprises a fat displacement field defining fat of the additional anatomy, wherein the displacement field comprises multi-dimensional displacement vectors and each of the displacement vectors relates a vertex of the skin mesh of the additional anatomy to a corresponding vertex of the fascia mesh of the additional anatomy, and wherein the parameterizing of the new anatomy comprises:

generating external parameters by parameterizing an exterior of each of the new anatomy and the additional anatomies by performing principal components analysis on vertex positions of the skin meshes of the new anatomy and the additional anatomies to determine body eigenvectors for each of the new and additional anatomies;

generating internal parameters by parameterizing an interior of each of the new anatomy and the additional anatomies by performing principal components analysis on the displacement fields of the new anatomy and the additional anatomies to determine fat eigenvectors for parameterizing the fat of each of the new anatomy and the additional anatomies; and adding the internal parameters and the external parameters to the database.

5. The non-transitory computer-readable storage medium of claim 1, wherein the adding the new anatomy to the database comprises:

for each of the additional anatomies, determining an exterior difference and an interior difference between an external parameter and internal parameter of the new anatomy and an external parameter and internal parameter, respectively, of the additional anatomy and comparing the exterior difference and the interior difference to a combined parameter threshold; and adding the new anatomy to the database based on the combined parameter threshold being satisfied for one or more of the additional anatomies.

6. The non-transitory computer-readable storage medium of claim 1, further comprising:

accessing the database storing additional anatomies; and interpolating the new anatomy from the additional anatomies.

7. The non-transitory computer-readable storage medium of claim 6, wherein the interpolating of the new anatomy comprises:

interpolating, using an external parameter characterizing an exterior of the new anatomy, vertices of a skin mesh of the new anatomy;

interpolating, from the database and an internal parameter characterizing fat of the new anatomy, a fat displacement field of the new anatomy comprising multidimensional displacement vectors, wherein each of the displacement vectors relates a vertex of the skin mesh to a corresponding vertex of a fascia mesh of the new anatomy; and determining the fascia mesh of the anatomy by subtracting the fat displacement field from the vertices of the skin mesh.

8. The non-transitory computer-readable storage medium of claim 7, further comprising:

interpolating the vertices of the skin mesh using an external starting vector, the external parameter, and body eigenvectors parameterizing exteriors of the additional anatomies; and interpolating the fat displacement field using an internal starting vector, the internal parameter, and fat eigenvectors parameterizing fat of the additional anatomies.

9. The non-transitory computer-readable storage medium of claim 7, further comprising, after the fascia mesh of the new anatomy is determined, transferring muscle and bone meshes from a template anatomy to the new anatomy.

10. The non-transitory computer-readable storage medium of claim 6, wherein the interpolating of the new anatomy comprises:

obtaining a skin mesh of the new anatomy that is in correspondence with a skin mesh of a template anatomy;

determining an external parameter characterizing an exterior of the new anatomy using vertices of the skin mesh of the new anatomy and body eigenvectors determined using vertices of skin meshes of the additional anatomies;

determining an internal parameter characterizing fat of the new anatomy by using regression based on the external parameter;

interpolating, from the database and using the external parameter, vertices of an interpolated skin mesh of the new anatomy;

interpolating, from the database and using the internal parameter, a fat displacement field of the new anatomy comprising multi-dimensional displacement vectors wherein each of the displacement vectors relates a vertex of the skin mesh to a corresponding vertex of a fascia mesh of the new anatomy;

determining an interpolated fascia mesh of the new anatomy by subtracting the fat displacement field from the vertices of the interpolated skin mesh; and determining the fascia mesh of the new anatomy by transferring the interpolated fascia mesh to the new anatomy.

11. The non-transitory computer-readable storage medium of claim 10, further comprising, after the fascia mesh of the new anatomy is determined, transferring muscle and bone meshes from a template anatomy to the new anatomy.

12. The non-transitory computer-readable storage medium of claim 6, wherein the interpolating of the new anatomy comprises:
obtaining a skin mesh of the new anatomy that is in correspondence with a skin mesh of a template anatomy;
determining an external parameter characterizing an exterior of the new anatomy using vertices of the skin mesh of the new anatomy and a body eigenvector determined using vertices of skin meshes of additional anatomies in a database;
determining k nearest neighbors to the external parameter in the database and weights for the nearest neighbors;
determining a weighted external parameter and a weighted internal parameter from the k nearest neighbors and the weights;
interpolating, from the database and using the weighted external parameter, vertices of an interpolated skin mesh of the new anatomy;
interpolating, from the database and using the weighted internal parameter, a fat displacement field of the new anatomy comprising multi-dimensional displacement vectors, wherein each of the displacement vectors relates a vertex of the skin mesh to a corresponding vertex of a fascia mesh of the new anatomy;
determining an interpolated fascia mesh of the new anatomy by subtracting the fat displacement field from the vertices of the interpolated skin mesh; and
determining the fascia mesh of the new anatomy by transferring the interpolated fascia mesh to the new anatomy.

13. The non-transitory computer-readable storage medium of claim 12, further comprising, after the fascia mesh of the new anatomy is determined, transferring muscle and bone meshes from a template anatomy to the new anatomy.

14. The non-transitory computer-readable storage medium of claim 6, wherein the interpolating of the new anatomy comprises:
obtaining a skin mesh of the new anatomy that is in correspondence with a skin mesh of a template anatomy;
determining k nearest neighbors to the skin mesh of the new anatomy and weights for the nearest neighbors; and
determining a fascia of the new anatomy by weight summing fascia meshes of the nearest neighbors.

15. The non-transitory computer-readable storage medium of claim 14, further comprising, after the fascia mesh of the new anatomy is determined, transferring muscle and bone meshes from a template anatomy to the new anatomy.

16. The non-transitory computer-readable storage medium of claim 14, further comprising determining at least one of bone meshes of the new anatomy by weight summing bone meshes of the nearest neighbors and muscle meshes of the new anatomy by weight summing muscle meshes of the nearest neighbors.

17. A system comprising:
one or more computer processors;
one or more computer memories;
a set of instructions incorporated into the one or more computer memories, the set of instructions configuring the one or more computer processors to perform operations, the operations comprising:
transferring a fascia mesh of the template anatomy to the new anatomy;
generating a fat displacement field defining fat of the new anatomy, the displacement field comprising multi-dimensional displacement vectors, each of the displacement vectors relating a vertex of the skin mesh of the new anatomy to a corresponding vertex of the fascia mesh of the new anatomy;
parameterizing the new anatomy relative to additional anatomies, a skin mesh and a fascia mesh of each of the additional anatomies in correspondence with the skin mesh and the fascia mesh of the new anatomy; and
adding the new anatomy to a database based on a comparison of one or more parameters of the new anatomy with one or more parameters of the additional anatomies.

18. The system of claim 17, the operations further comprising:
accessing the database storing additional anatomies; and
interpolating the new anatomy from the additional anatomies.

19. A method for storing a set of instructions that, when executed by one or more computer processors, cause the one or more computer processors to perform operations, the operations comprising:
transferring a fascia mesh of the template anatomy to the new anatomy;
generating a fat displacement field defining fat of the new anatomy, the displacement field comprising multi-dimensional displacement vectors, each of the displacement vectors relating a vertex of the skin mesh of the new anatomy to a corresponding vertex of the fascia mesh of the new anatomy;
parameterizing the new anatomy relative to additional anatomies, a skin mesh and a fascia mesh of each of the additional anatomies in correspondence with the skin mesh and the fascia mesh of the new anatomy; and
adding the new anatomy to a database based on a comparison of one or more parameters of the new anatomy with one or more parameters of the additional anatomies.

20. The method of claim 19, the operations further comprising:
accessing the database storing additional anatomies; and
interpolating the new anatomy from the additional anatomies.

* * * * *